(12) United States Patent
Zart et al.

(10) Patent No.: US 7,309,262 B2
(45) Date of Patent: Dec. 18, 2007

(54) CONNECTOR ASSEMBLY FOR AN IMPLANTABLE MEDICAL DEVICE AND PROCESS FOR MAKING

(75) Inventors: Bryan J. Zart, Shakopee, MN (US); Andrew J. Ries, Lino Lakes, MN (US); Brian R. Burwick, Guntersville, AL (US); John E. Nicholson, Blaine, MN (US); Jay K. Lahti, Shoreview, MN (US); Gregory A. Theis, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/668,260

(22) Filed: Jan. 29, 2007

(65) Prior Publication Data

US 2007/0190866 A1 Aug. 16, 2007

Related U.S. Application Data

(60) Continuation-in-part of application No. 10/966,636, filed on Oct. 15, 2004, now Pat. No. 7,175,482, which is a division of application No. 09/885,354, filed on Jun. 20, 2001, now Pat. No. 6,817,905.

(60) Provisional application No. 60/212,746, filed on Jun. 20, 2000.

(51) Int. Cl.
*H01R 13/405* (2006.01)

(52) U.S. Cl. .......................... 439/736; 439/909; 607/36

(58) Field of Classification Search ............... 439/736, 439/909; 607/36, 37; 29/841; 264/36
See application file for complete search history.

(56) References Cited

U.S. PATENT DOCUMENTS

| | | | |
|---|---|---|---|
| 4,113,627 A | 9/1978 | Leason | |
| 4,884,980 A | 12/1989 | Bensing et al. | |
| 4,983,344 A | 1/1991 | Brown | |
| 5,098,769 A | 3/1992 | Nakai et al. | |
| 5,342,408 A * | 8/1994 | deCoriolis et al. | 607/32 |
| 5,453,029 A | 9/1995 | Moldenhauer et al. | |
| 5,679,026 A | 10/1997 | Fain et al. | |
| 5,851,221 A * | 12/1998 | Rieder et al. | 607/93 |
| 6,205,358 B1 | 3/2001 | Haeg et al. | |
| 6,456,256 B1 * | 9/2002 | Amundson et al. | 343/873 |
| 6,792,312 B2 * | 9/2004 | Bruchmann et al. | 607/37 |
| 6,799,072 B2 * | 9/2004 | Ries et al. | 607/36 |
| 6,884,122 B2 * | 4/2005 | Robinson et al. | 439/722 |
| 7,016,733 B2 * | 3/2006 | Dublin et al. | 607/36 |
| 2005/0245884 A1 * | 11/2005 | Deininger | 604/247 |

* cited by examiner

*Primary Examiner*—Michael C. Zarroli
(74) *Attorney, Agent, or Firm*—Michael C. Soldner

(57) ABSTRACT

A connector assembly for coupling to an implantable medical device includes a core element formed of a first thermoplastic material shaped to receive a connector member for receiving a lead. The connector assembly further includes a circuit member positioned adjacent to the core element. The circuit member includes a portion extending along the core element to the connector member and an antenna structure extending over a portion of the core element outer surface.

12 Claims, 20 Drawing Sheets

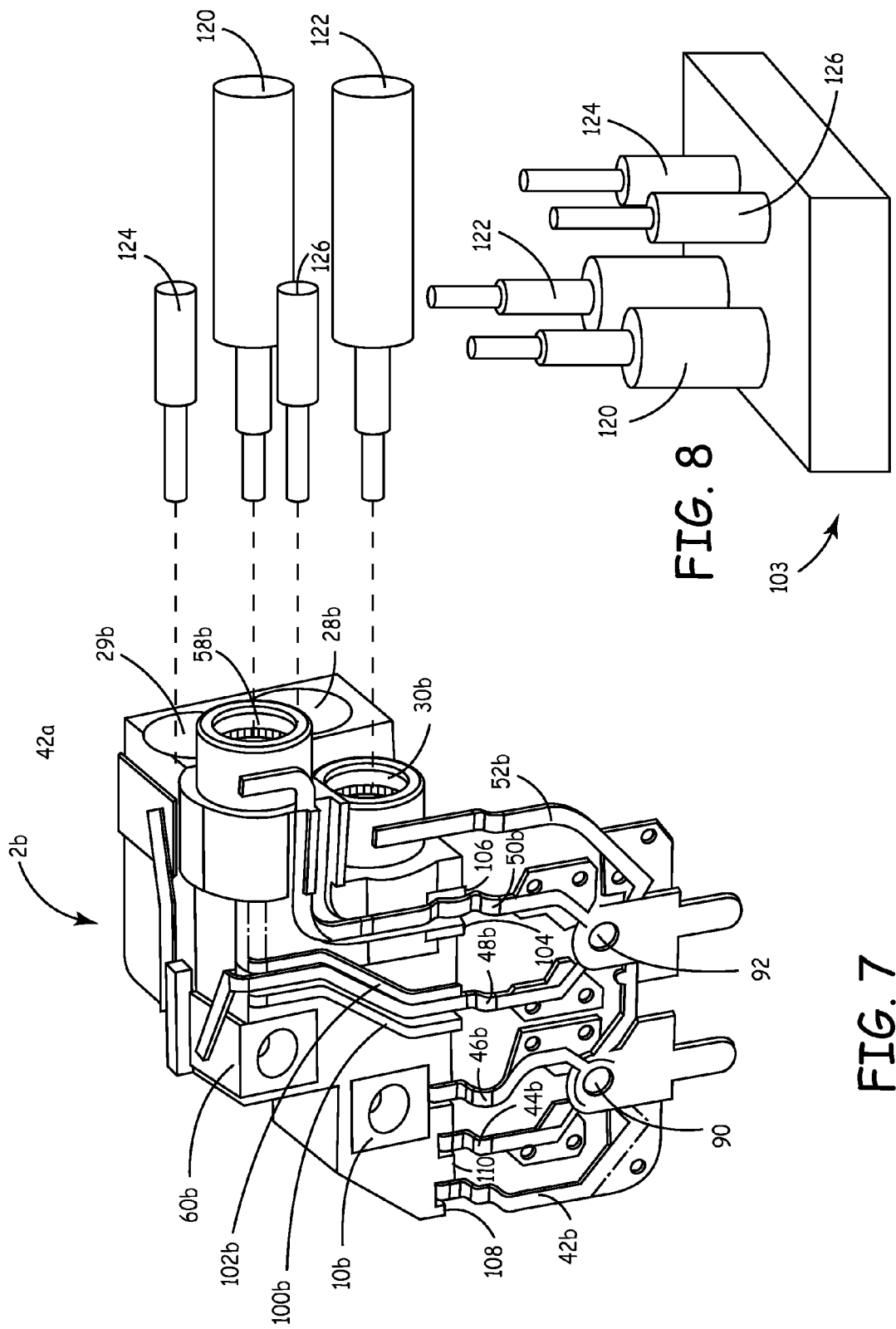

CONNECTOR ASSEMBLY FOR AN IMPLANTABLE MEDICAL DEVICE AND PROCESS FOR MAKING

RELATED APPLICATIONS

This application is a continuation-in-part (CIP) of Appl. No. 10/966,636, now U.S. Pat. No. 7,175,482, filed on Oct. 15, 2004, which is a divisional of U.S. Pat. No. 6,817,905, filed on Jun. 20, 2001, which claims priority to U.S. Provisional Application No. 60/212,746, incorporated herein by reference in its entirety.

TECHNICAL FIELD

This invention relates to a process for molding a circuit component; and more particularly, to a two-shot thermoplastic molding process for manufacturing an electrical connector.

BACKGROUND

Electrical connectors and other similar electrical components often include electrical conductors embedded within an insulating housing to isolate the conductor from the surrounding environment. Embedding the conductor within a housing protects the conductor from damage, and also prevents the delivery of an electrical shock. Electrical isolation is particularly important when the connector is to be coupled to an implantable medical device such as a pacemaker or defibrillation system.

One way to form an electrical connector having conductors embedded therein is to mold a solid set-screw block using injection molding techniques. After the molding is completed, the surface of the set-screw block is formed to include channels. Wires or other types of connectors are pressed into the channels. Generally, each end of each wire is welded to some type of electrical contact. An insulating adhesive is then applied over the wires and channels. If the connector is to be used with an implantable medical device, a medical adhesive is often employed for this purpose. The adhesive is cured to form a protective, insulating layer that isolates the wires from external elements.

Although the afore-mentioned method is relatively straight-forward, it requires manual application of the adhesive. This introduces variables into the manufacturing process. If the adhesive is not properly dispensed, some portions of the conductor may become exposed. As a result, shorts may develop between adjacent conductors. Additionally, a conductor may come in contact with external elements, causing degradation and loss of conductive capabilities. Moreover, because a manual process is employed, the manufacturing mechanism is relatively time-consuming and expensive.

An alternative approach to the use of adhesives involves the positioning of one or more conductors within a mold in some predetermined orientation. An insulating plastic is then introduced into the mold to encapsulate the conductors. The plastic hardens to provide the necessary insulating layer around the conductors. While this process eliminates the variables associated with a manual step, it is nevertheless difficult to implement with other than a simple design. This is because the introduction of the plastic into the mold at high pressures generally causes the position of the conductors to shift. This may result in shorts between multiple conductors, or conversely, may result in loss of a desired electrical connection. While plastic injection systems of this nature generally include mechanisms to hold the conductors in place during the injection process, the process is more prone to failure than other methods because shifting of components may occur regardless of the efforts to prevent it. Additionally, a more complex tooling system is required to implement the process. Finally, the difficulty associated with maintaining isolation between multiple conductors places limits on the assembly dimensions. That is, an assembly cannot be made too small because shorts will occur between closely spaced conductors that shift during the mold injection process.

Yet another approach used to create connector assembly includes use of a two-step thermoset casting process. A first mold is used to receive a thermoset plastic material such as an epoxy. As is known in the art, a thermoset plastic hardens because of a chemical reaction occurring between the various components of the plastic material. After the curing process is complete, the first molded connector element is removed from the mold. Conductors are selectively positioned on the exterior of this first element. The first element is then positioned within a second mold and a thermoset material is selectively applied to the first element to encapsulate the conductors.

The two-step thermoset process provides a mechanism for embedding conductors within a connector in a more precise manner. This is because the first element holds the conductors in position while the second molding step is performed. However, because thermoset material requires a relatively long time to cure, the process is slow. The manufacture time is increased since two serial curing steps are required. Moreover, because the final products may not be removed from the molds until the curing is completed, many molds must be employed to increase output.

What is needed, therefore, is an improved mechanism for creating more complex connector structures using a faster production cycle.

BRIEF DESCRIPTION OF THE DRAWINGS

FIG. 7 is a side perspective view of circuit member positioned on the surface of core element.

FIG. 8 is a front perspective view of a lead core assembly.

DETAILED DESCRIPTION

Figure 1:
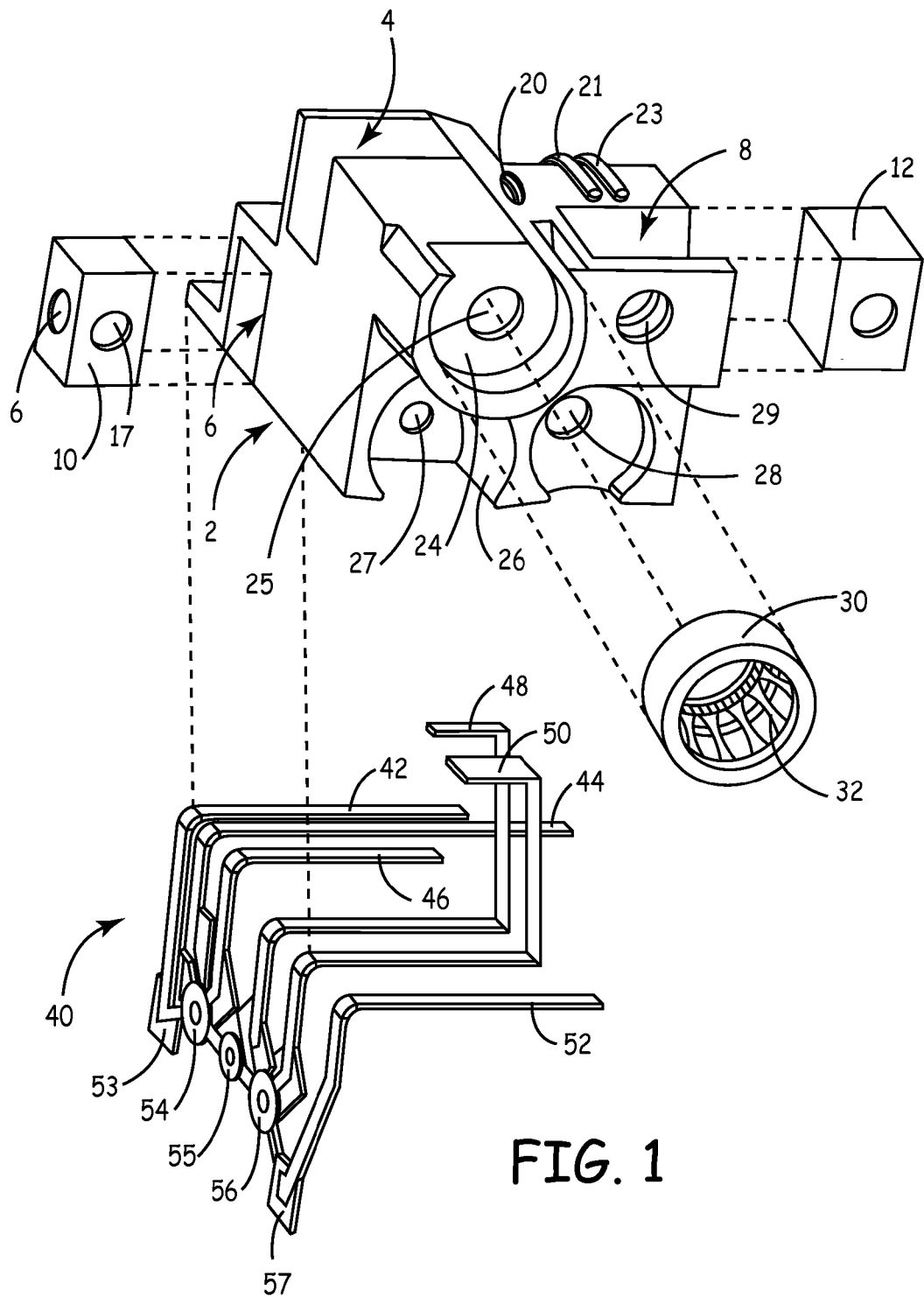
FIG. 1 is a front perspective view of a connector core element of one embodiment of the current invention.

FIG. 1 is a front perspective view of a connector core element 2 of one embodiment of the current invention. Core element is integrally formed of a biocompatible thermoplastic material, which may be a polyurethane such as pellathane commercially available from The Polymer Technology Group (PTG) Incorporated, or Tecothane® commercially available from Thermedics Incorporated. Other polyurethane materials are suitable for use in the current inventive process, as are other thermoplastic materials such as polysulfone. In one embodiment, a suitable biocompatible polyurethane may have a hardness of between 50 D and 90 D (Shore), and is preferably about 75 D.

The core element 2 is formed by heating the thermoplastic material to a temperature that is at, or slightly above, the melt point. The material is then injected into a primary mold formed into the desired shape of the core element and allowed to cool. Cooling is generally completed in between twenty to seventy seconds. This is much shorter than the curing period for thermoset materials, which may be as much as one hour. After cooling, core element 2 is removed from the mold. The removal process involves opening the mold, which includes an ejection mechanism that automatically releases the core element.

Core element 2 may take many different shapes. In one embodiment, core element includes a structure that supports various metal piece parts in a stable manner that can be maintained during a second-shot molding process to be discussed below. In the embodiment of FIG. 1, core element 2 includes receptacles 4, 6, and 8. Each of the receptacles is adapted to receive a respective set-screw block, such as set-screw block 10 to be inserted within receptacle 6, and set screw block 12 to be inserted within receptacle 8. Receptacle 4 is adapted to receive a similar set-screw block not shown in FIG. 1 for purposes of simplification. Set-screw blocks may be formed entirely, or partially, from a conductive material such as MP35N, stainless steel or titanium.

The set-screw blocks are loosely maintained within a respective receptacle by the shape of core element 2 until the second-shot over-molding process is completed. Each of these set-screw blocks includes an opening such as opening 16 to receive a set screw, and a second opening such as opening 17 to receive the pin or ring connector provided at the proximal end of a medical lead. A set screw inserted within opening 16 is used to mechanically couple to a lead connector pin or ring to hold the lead in place, as will be described further below.

In an alternative embodiment, the various receptacles need not be included and the set-screw blocks may be integrally formed within the core element by positioning the set-screw blocks with the primary mold prior to injecting the thermoplastic material to form core element 2. In this instance, sealing means must be provided to prevent the thermoplastic from being injected into the openings of the set-screw blocks. For example, the primary mold could include peg members adapted to be loaded into the openings of set-screw blocks so that a tight seal is formed prior to injecting the thermoplastic into the mold. The pegs would also retain the set-screw blocks in position during the high-pressure injection process.

Returning to FIG. 1, core element 2 also includes additional circular receptacles 24 and 26. Each circular receptacle includes an aperture 25 and 27, respectively, to receive the connector pin of a medical electrical lead. For example, during use, a lead connector pin may be inserted within aperture 25 and further through opening 17. The lead is held in place by a fastening member inserted within opening 16 of set-screw block 10 and tightened on the lead pin or ring as is known in the art.

In the embodiment shown, each circular receptacle 24 and 26 is adapted to receive a respective connector member such as connector member 30. This type of connector member may be formed entirely or partially of a conductive material such as stainless steel or titanium. Connector member 30 is shown to include a multi-beam connector (MBC) 32 adapted to couple electrically and mechanically to a ring connector of a bipolar medical electrical lead. This type of connector member would support a lead having a connector conforming to the IS-1 standard, for example. Other types of connector members may be utilized to form an electrical and/or mechanical connection, as is known in the art.

In an alternative embodiment, the connector members may be eliminated by integrally forming the connectors such as connector member 30 within core element 2. This may be accomplished by loading the primary mold with the connectors prior to injecting the thermoplastic. As discussed above with respect to the set-screw blocks, some mechanism must be provided to prevent the thermoplastic from flowing over the conductive surface of the connectors. Additionally, the connector members must be retained in position during the high-pressure injection process.

Core element 2 further includes additional lead bores 28 and 29 to receive the connector pins of additional leads. These lead bores may be adapted to couple to the pin of a lead conforming to the DF-1 standard for medical electrical leads, for example. Additional apertures such as apertures 20 may be provided to couple to additional circuit components in a manner to be discussed below. Core element may further have one or more guide members shown as guide members 21 and 23 integrally formed on the surface of core element 2. These guide members serve as support and positioning mechanisms for the additional circuit components, and also improves the overmolding process, as is described below.

FIG. 1 further illustrates a circuit member 40 which is formed of a conductive material such as stainless steel, titanium, niobium, tantalum, or any other conductive biocompatible conductive material. Circuit member 40 includes multiple conductive traces or finger elements 42 through 52, each extending to a respective connector pads 53 through 57. When the circuit member 40 is initially coupled to core member 2, connector pads may be electrically and mechanically joined to make the assembly process more efficient. Circuit member 40 may be soldered or welded to the various metal piece parts associated with core element 2, including set-screw blocks 10 and 12, and the various connector members 30 in a manner to be discussed below.

As noted above, using a single circuit member 40 having conductive finger elements that are mechanically and electrically joined makes the initial assembly process easier since multiple elements need not be loaded onto the core element 2. However, in this embodiment, an additional step is required later in the assembly process to electrically isolate these components, as will be discussed below. In another embodiment, each of the multiple conductive finger elements 42 through 52 may be an individual circuit element that is not mechanically or electrically coupled to the other finger elements. In this embodiment, the multiple finger elements must be individually loaded onto the core element. However, the additional step of electrically isolating these components later is not required. In yet another embodiment, the conductive finger elements may be joined in a single circuit member via insolated material. In this embodiment, the circuit member is a unified structure that couples the conductive finger elements mechanically, but provides electrical isolation. In this embodiment, the additional step of electrically isolating these components later is not required.

In yet another embodiment, the circuit member 40 could be integrally formed to include the various connector members and set-screw blocks so that the soldering or welding process may be eliminated. Using this embodiment, attaching the circuit member 40 to the core element involves loading the receptacles and apertures of the core element with the set-screw blocks and connector members, respectively.

Figure 2:
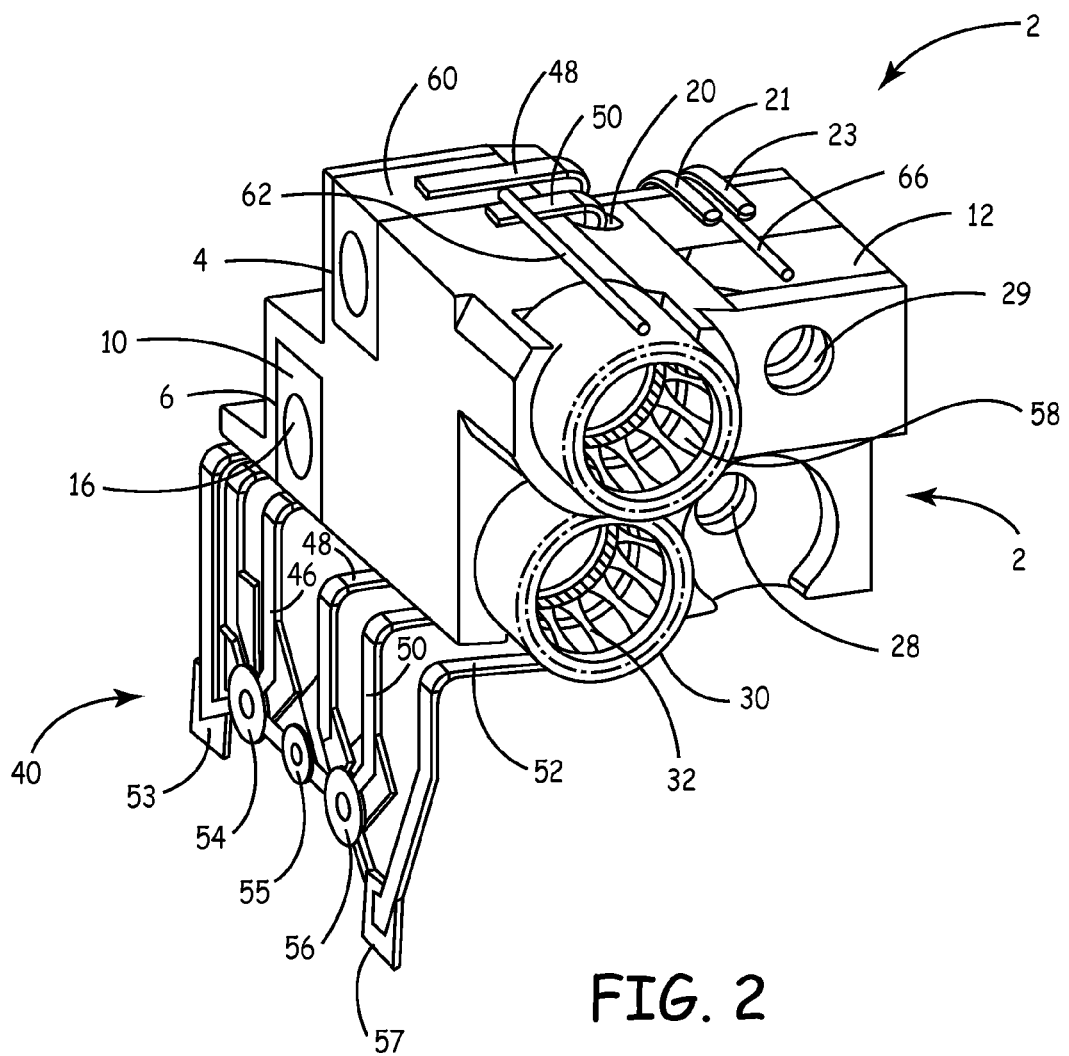
FIG. 2 is a front perspective view of a core member loaded with respective set-screw blocks and connector members.

FIG. 2 is a front perspective view of core member 2 with respective set-screw blocks inserted into receptacles 4, 6 and 8, and with connector members 58 and 30 inserted into circular receptacles 24 and 26. This view further illustrates circuit member 40 coupled to core member 2. In this embodiment, finger elements 48 and 50 of circuit member 40 may extend through apertures provided within core element 2. For example, finger element 50 is inserted through aperture 20, which is a channel that extends through the core member. Similarly, finger element 48 extends through an additional aperture (not shown in FIG. 2) to position circuit member in a precise location with respect to core element 2. In one manner of use, finger elements 48 and 50 are formed of a material that is deformable, and which may be temporarily straightened to be threaded through a respective aperture such as aperture 20. In another embodiment, finger elements 48 and 50 are initially straight, and may be manually or automatically bent in the manner shown in FIG. 2 after being inserted within a respective aperture.

After circuit member 40 is coupled to core member 2, it may be soldered or welded to form predetermined electrical and mechanical connections between connector members and set-screw blocks and respective ones of the conductive finger elements. For example, finger element 46 may be coupled to set-screw block 10, whereas finger element 48 is electrically coupled to set-screw block 60.

Additional circuit elements may further be coupled to the core element using soldering, welding, or any other appropriate process. For example, jumper 62 may be soldered or welded to both finger element 46 and connector member 58 to form an electrical connection between the two components. Jumper 66 may be positioned on the surface of core member 2 using guide members 21 and 23 to align the circuit member in a desired location so that an electrical connection may be formed between set-screw block 12 and a predetermined respective one of the finger elements.

Figure 3:
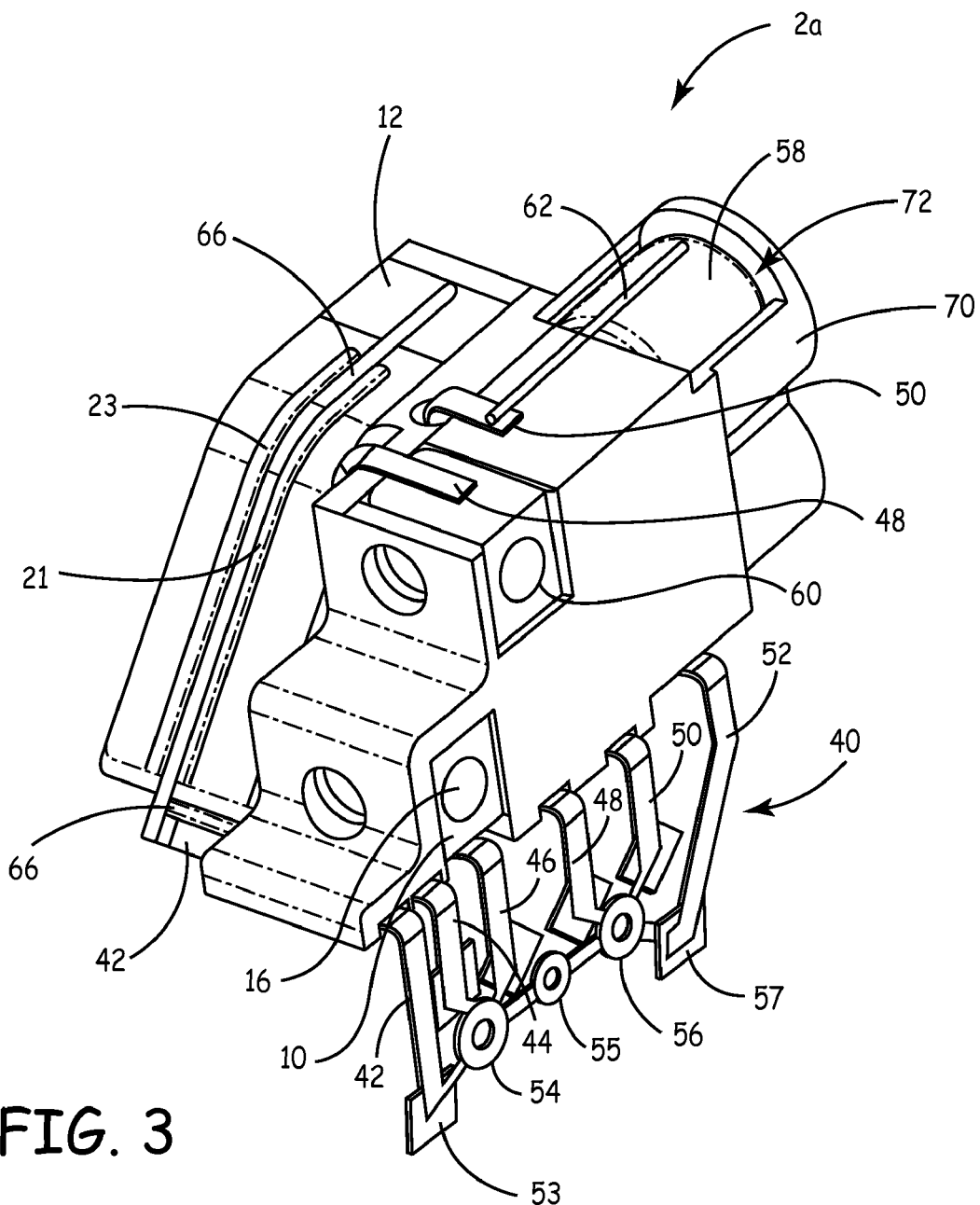
FIG. 3 is a back perspective view of an alternative embodiment of the core member.

FIG. 3 is a back perspective view of an alternative embodiment of the core member designated core member 2a. Although similar in almost every respect to the core members of FIGS. 1 and 2 discussed above, this core member includes a support structure 70 that is integrally molded into core element 2, and which is provided to receive and support connector members such as connector members 30 and 58. This support structure has a cutaway portion 72 to allow circuit element 62 to be welded or soldered to connector member 58. Although this support structure helps maintain the connector members in position during the second-shot overmolding process, it may make insertion of the connector members more cumbersome, and adds additional mass to the core element 2, which may be undesirable for reasons to be discussed further below.

FIG. 3 further illustrates the manner in which finger elements 48 and 50 of circuit member 40 are threaded through apertures of core member 2. Further illustrated is circuit element 66, which is maintained in position on the surface of core element by guide members 21 and 23 to form an electrical connection between set-screw block 12 and finger element 42.

Figure 4:
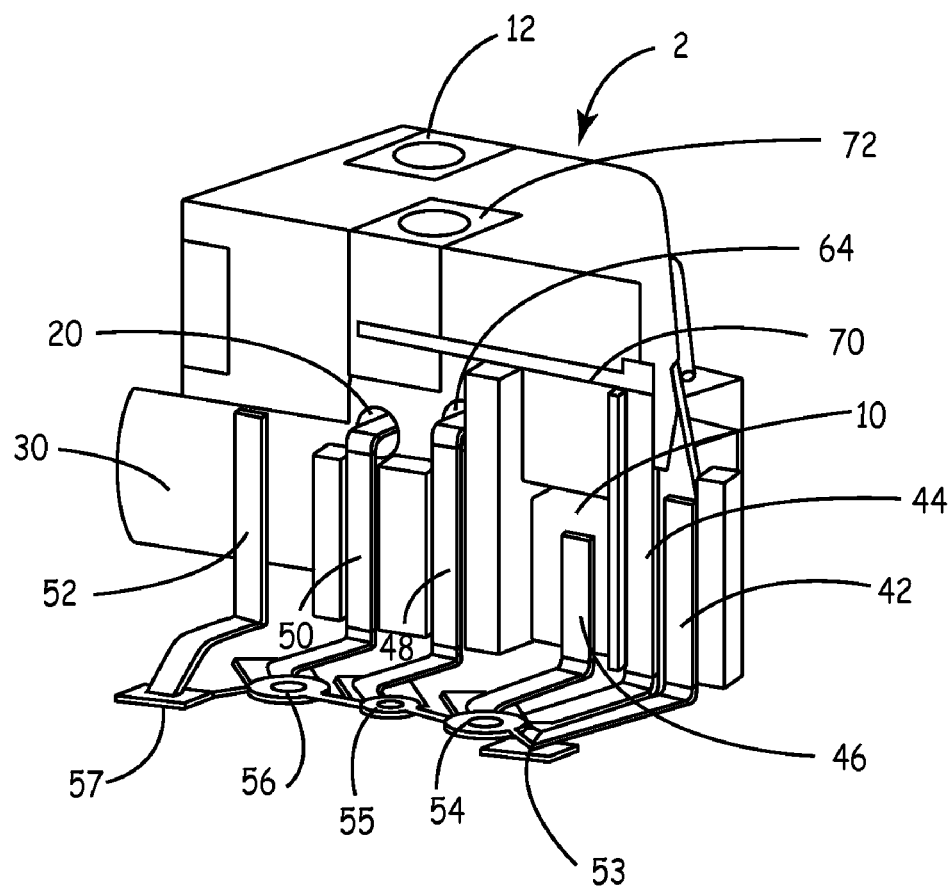
FIG. 4 is a bottom perspective view of core member.

FIG. 4 is a bottom perspective view of core member 2. This view illustrates the manner in which finger elements 48 and 50 extend through apertures 20 and 64, respectively. This view also shows the manner in which the various finger elements may be electrically coupled to connector members and set-screw blocks. For example, finger element 44 is jumpered via circuit element 70 to set-screw block 72; finger element 46 is electrically coupled to set-screw block 10, and so on.

As shown in FIG. 4, one manner of retaining circuit member 40 in position in proximity to core element 2 is through the use of apertures that extend through the core member and are adapted to receive respective finger elements of the circuit member 40. While this helps to prevent shifting of the circuit member 40 during the second-shot molding process, the process of threading the finger members through the various apertures is cumbersome and time-consuming.

Figure 5:
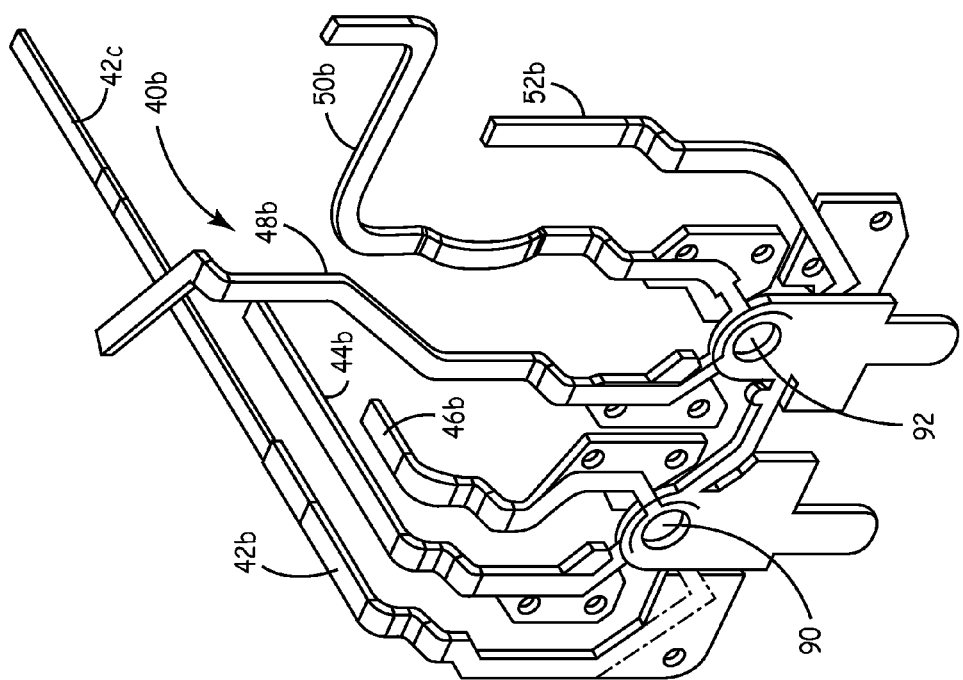
FIG. 5 is side perspective view of an alternative embodiment of the circuit member.

FIG. 5 is side perspective view of an alternative embodiment of the circuit member. In this view, like features of circuit member 40b as compared to circuit member 40 of FIGS. 1 through 4 are designated with like numeric identifiers including an additional suffix. This embodiment includes finger elements 44b through 46b that are not adapted to engage apertures in a core element. Instead, these elements are adapted to be placed externally on the surface of the core element to reduce assembly time prior to the second-shot overmolding step. One or more of the finger elements such as finger element 42b may have a longer, flexible conductive end. This end is adapted to be manually shaped to conform to a surface of the core member, as described below. FIG. 5 also illustrates the use of alignment apertures 90 and 92, which are provided to position the core element at a predetermined location within the second-shot mold to be discussed below.

Figure 6:
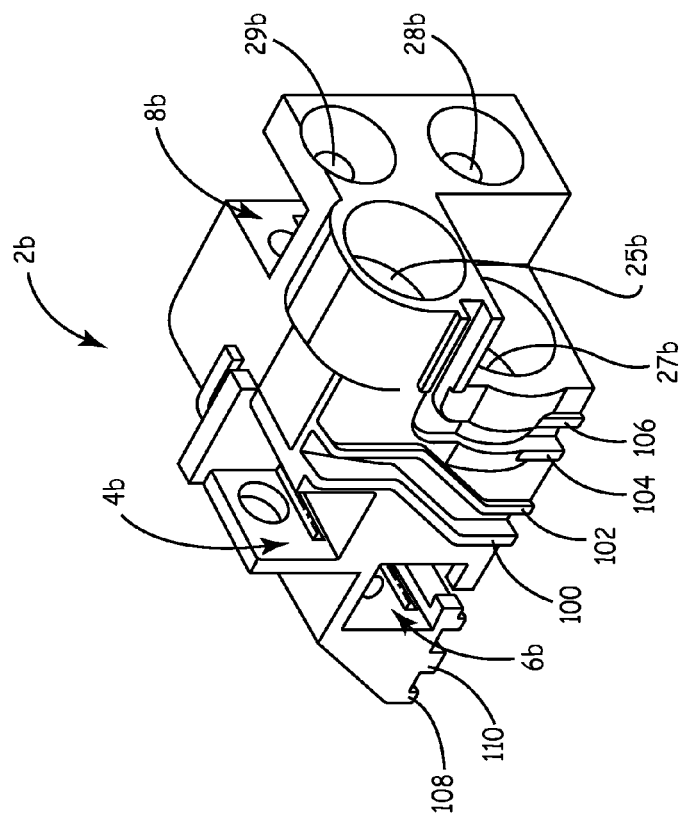
FIG. 6 is side perspective view of an alternative embodiment of the core element adapted to engage the circuit member of FIG. 5.

FIG. 6 is side perspective view of an alternative embodiment of the core element adapted to engage the circuit member 40b of FIG. 5. As in FIG. 5, like features of core element 2b as compared to core element 2 of FIGS. 1 through 4 are designated with like numeric identifiers including an additional suffix. Core element 2b includes channel guides such as channel guides 100 through 110 that are provided to guide the finger elements of circuit member 40b into the desired position on the surface of core element 2b. During the second-shot overmolding process, these channel guides retain the finger elements in position, and prevent shifting that may results in shorts between adjacent finger elements. These channel guides also promote integration of the material of the core element with the additional thermoplastic material provided during the overmolding process, as will be discussed further below.

FIG. 7 is a side perspective view of circuit member 40b positioned on the surface of core element 2b. This figure illustrates the manner in which finger elements are positioned using the guide members. For example, finger element 52b is positioned between guide members 104 and 106, and finger element 42b is positioned between guide members 108 and 110 provided on the bottom surface of core member 2b. The finger elements may be soldered or welded to the conductive components such as the set-screw blocks that are inserted in core member 2b in the manner discussed above. Other circuit elements may also be used to form electrical connections between circuit member 40b and a predetermined conductive component. Alternatively, the longer finger elements such a finger element 42b having a flexible elongated end 42c (FIG. 5) may be manually shaped into position and welded to form the desired connection as shown in FIG. 7. In this example, the end 42c of finger element 42b is shaped along the top surface of core member 2c to electrically couple to set-screw block 12c. This use of longer conductive finger elements makes the assembly process more efficient by eliminating the need for additional circuit components, and by minimizing the number of locations that must be welded or soldered.

After all conductive components have been inserted into the core element and the circuit member 40b has been welded, soldered, or otherwise fixed into place, the resulting core element assembly may be prepared to undergo the second-shot overmolding process. This preparation may involve inserting pin members into the connector members and the apertures of the set-screw blocks so that thermoplastic material does not fill these structures during the overmolding process. FIG. 7 illustrates pin members 120 and 122 being inserted into connector members 58b and 30b, respectively. Pin members 124 and 126 are similarly inserted into lead bores 29b and 28b, respectively. Additional pin members or bushings (not shown in FIG. 7 for clarity) may be inserted into the apertures of each of the set-screw blocks of core element 2b. These pin members are made of a material that will withstand the temperature and pressure conditions associated with the injection molding process. For example, the pin members may be made of a tool steel or another type of stainless steel. In one embodiment, multiple ones of the pin members may be incorporated into a core assembly structure to make insertion into the core element easier.

FIG. 8 illustrates an lead core assembly 130, which is assembly that provides the pin members 120 through 126 shown in FIG. 7. The lead core assembly aligns the pin members, and allows them to be inserted in one step.

In an alternative embodiment, ones of the pin members such as those inserted into the set-screw blocks may be eliminated by using protrusions in the second-shot mold assembly. These protrusions are inserted into the set-screw blocks as the core element is placed within the mold and the mold is closed, thereby eliminating the step of manually inserting the pin members into the core element. This is discussed further below.

Figure 9:
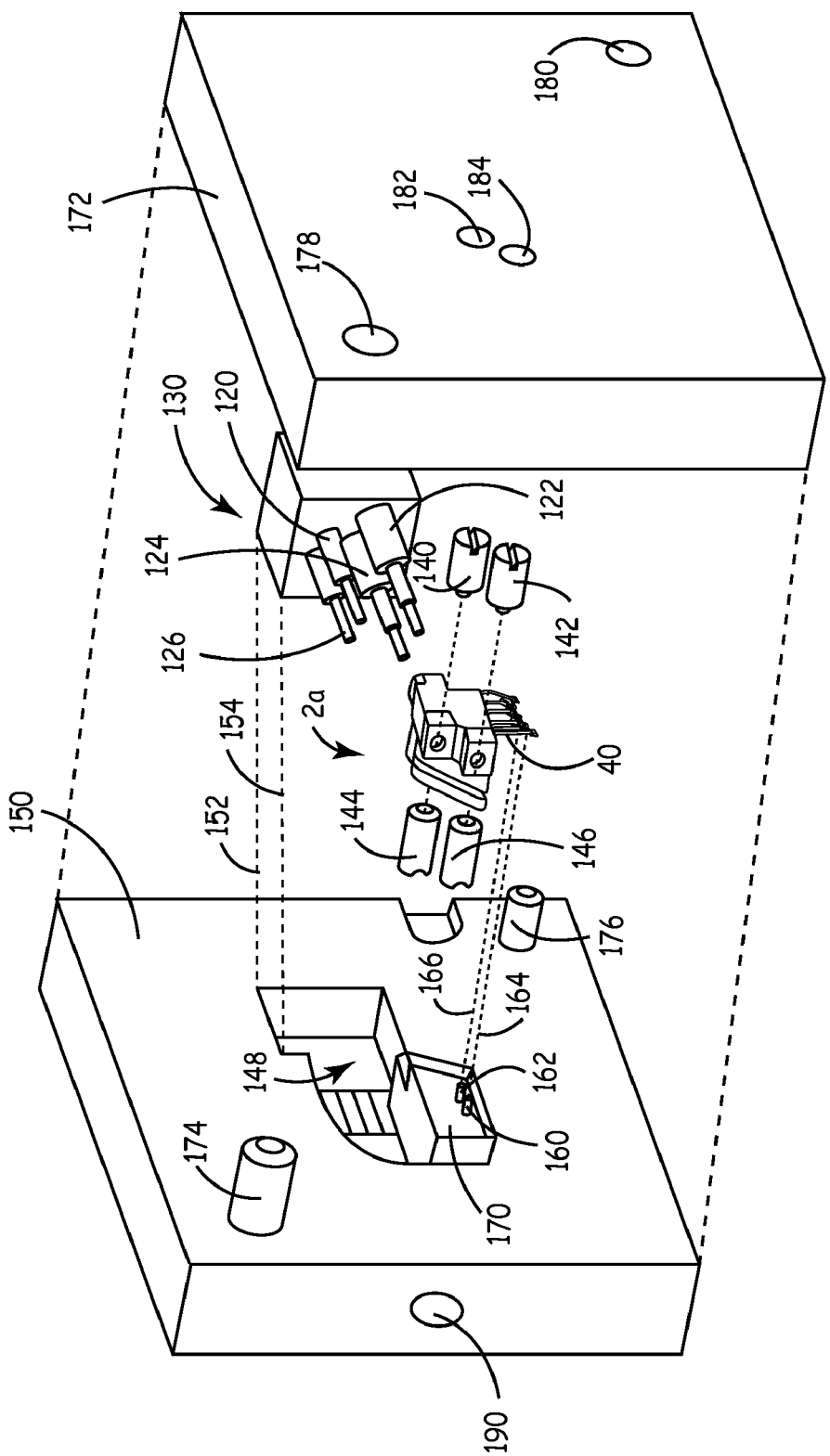
FIG. 9 is a perspective view of a core element being prepared for the overmolding process.

FIG. 9 is a perspective view of a core element being prepared for the overmolding process. This view, which is similar to that shown in FIG. 3, illustrates core member 2a and the associated metal piece parts that have been loaded into the core member. Lead core assembly 130 is utilized to insert pin members 120, 122, 124, and 126 into the respective structures of the core element as discussed in reference to FIG. 8. Similar bushings 140, 142, 144 and 146 may be inserted into the apertures of the set-screw blocks. As noted above, bushings 144 and 146 may be eliminated by instead providing protrusions within cavity 148 of the bottom portion 150 that are aligned with the set-screw blocks. Similar protrusions may be provided in the top portion 172 of the mold to replace bushings 140 and 142. Providing such structures in the mold itself eliminates the requirement of manually loading the bushings into the core element.

After the core element is prepared for the overmolding process, the entire assembly may then be loaded into cavity 148 of a bottom portion 150 of a second-shot mold fixture. The lead core assembly is positioned within the mold as shown by dashed lines 152 and 154. In this position, the lead core assembly suspends the core element within the cavity of the mold so that the surface of the core element is not in contact with the interior surface of the mold. The positioning of the core assembly may further be aided by fitting predetermined ones of the apertures included in the circuit member 40 with the alignment pins 160 and 162 of the mold as illustrated by dashed lines 164 and 166. For example, the apertures in connector pads 54 and 56 of circuit member 40 (FIGS. 2 and 3) or the alignment apertures 90 and 92 (FIG. 5) could be used for this purpose. The circuit member 40 may further be supported by a shoulder member 170.

After the assembly has been properly aligned within the bottom portion 150, the top portion 172 of the second-shot mold fixture is aligned with the bottom portion. This may be accomplished by inserting pegs 174 and 176 into channel members 178 and 180. Both top and bottom mold portions may include additional channels such as channels 182 and 184 to accommodate set-screws 140 and 142, respectively. Similar channels may be provided in the bottom portion 150 of the mold fixture.

When the bottom and top portions of the mold fixture have been aligned, a press may be utilized to maintain the alignment during the high-pressure injection procedure. A thermoplastic material is heated to at least the melting temperature, or preferably, slightly above the melting temperature, of the material, and is injected into cavity 148 via injection port 190. The same, or a different, thermoplastic material may be used in the second-shot injection process as compared to that used in the core element. Moreover, the second-shot material may entirely encapsulate the core element, or alternatively, need only cover a portion of the core element. For example, it may be desirable to leave exposed a portion of the thermoplastic material included in the core element in the region of the circuit member connector pads.

During the second-shot injection process, it is important to ensure that bonding occurs between the core element and the second shot material. If bonding does not occur, very small amounts of ionic liquid pool between the core element 2 and the overmold material after the connector has been implanted within a living body for an extended period of time. This may result in what is an unacceptably large leakage current between adjacent finger elements of the circuit element. One way to ensure that adequate bonding is achieved is to heat the second-shot plastic as hot as the material characteristics will allow, and to inject the material as quickly as possible. This allows the core element to be heated by, and thereafter bonded to, the second-shot material.

Another method used to enhance the bonding process is to ensure that the mass of the core element is as small as possible. This allows the core element to be heated sufficiently during the overmold process. In one embodiment, the mass of the thermoplastic material incorporated into the core element is less than half of the mass of the material utilized during the overmold process, and is preferably less than thirty percent of that of the overmold structure.

Another mechanism for enhancing the bonding of the core element to the overmold material involves heating the core element prior to injecting the second shot of thermoplastic material. If this method is utilized, the mass of the core element may be greater while still achieving adequate bonding. This is because the second shot of thermoplastic material is not providing all of the heat needed to warm the core element, with at least some of the heat being provided during the heating step that precedes the injection step. In one embodiment, the mass of the core element is greater than fifty percent of the thermoplastic material used during the overmold process while still retaining adequate bonding.

Integration of the core element with the overmold material may be further enhanced by providing relatively thin protruding structures to the core member surface. Because these relatively thin structures are readily melted and integrated with the second-shot material, integration of the core element with the overmold structure is enhanced. For example, guide members 100 through 110 (FIG. 6) serve not only to guide circuit elements on the surface of the core member, but also facilitate this type of bonding between the core element 2 and the overmold material. In one embodiment, additional thin fin-like structures may be provided in arbitrary shapes along various surfaces of the core member to facilitate additional integration. Such structures may be included in the first-shot mold assembly. Although such structures do enhance integration, the addition of such structures makes the molding of the core element more complex.

Following the injection of the overmold material, the entire assembly is allowed to cool for twenty to seventy seconds, depending on the type of thermoplastic material utilized as determined by the manufacturer specifications. The top portion of the mold is removed from the bottom portion, causing the finished connector assembly to be released. After removal from the mold, the connector pads of the circuit member 40 may be separated, if necessary, to achieve electrical isolation, as may be performed by cutting away the intervening conductive traces. The pads may then be soldered or welded to respective connectors of an implantable medical device such as a pacemaker or cardioverter/defibrillator, and overlaid with a medical adhesive to maintain electrical isolation in the connection area. It may be noted that if individual circuit elements are utilized in place of circuit member 40 or 40*b*, the step of removing the intervening conductive traces between finger elements may be eliminated.

Figure 10:
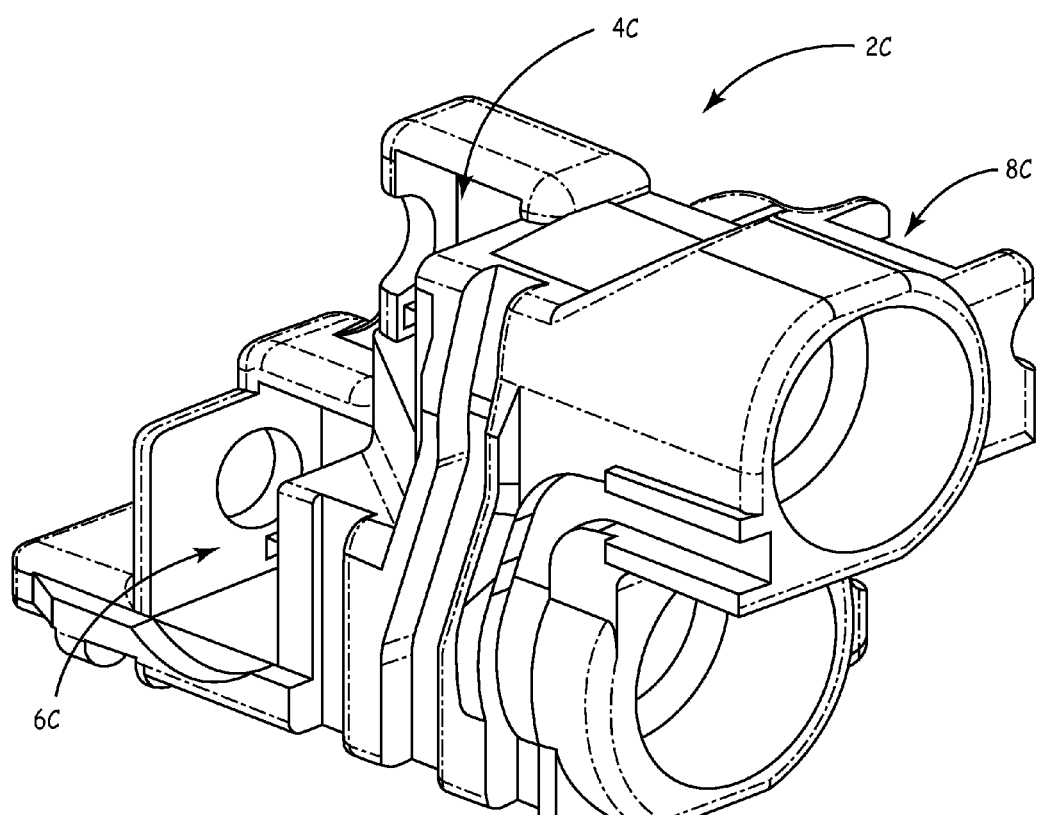
FIG. 10 is a side perspective view of an alternative embodiment of a core element which is designed to minimize core element mass.

As discussed in the foregoing paragraphs, one way to promote the formation of an adequate bond between the core member and the overmold material is to utilize a core element that is as small as possible. An alternative embodiment of a core element directed to minimizing core element mass is shown in FIG. 10. It may be noted that in this embodiment, the walls defining receptacles 4*c*, 6*c*, and 8*c* are relatively thin structures as compared to similar structures shown in FIGS. 1 and 6. Other structure adjacent to receptacle 8*c* has also been eliminated.

Figure 11:
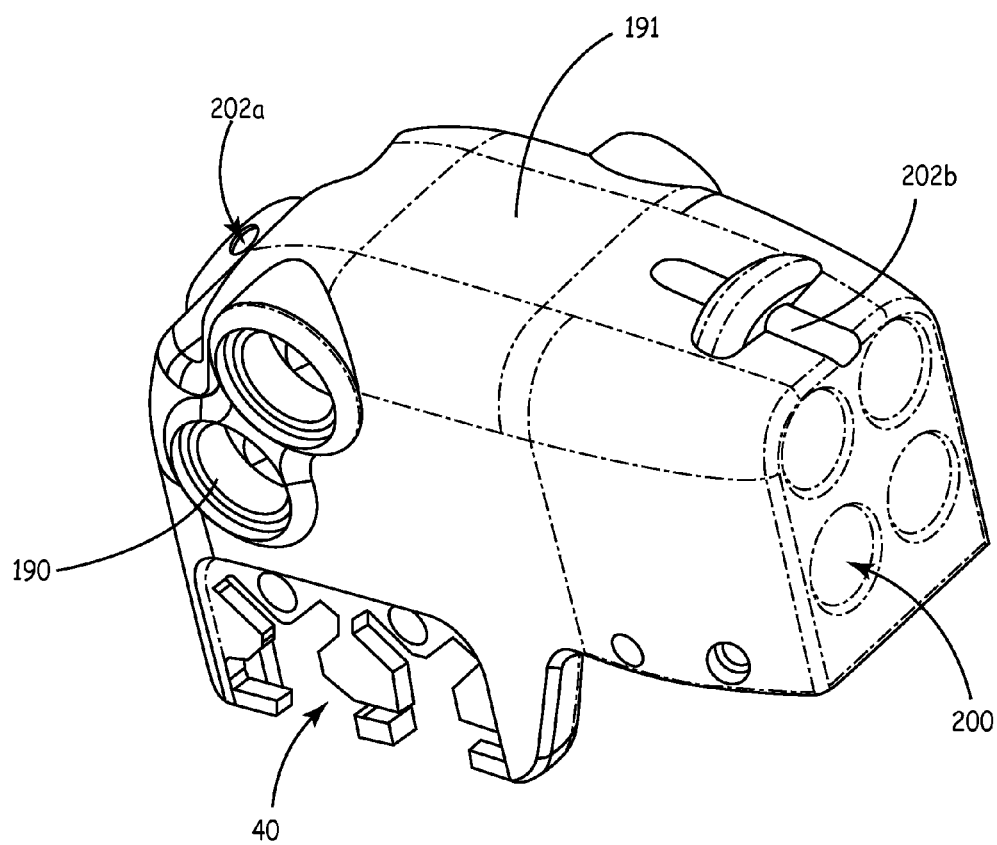
FIG. 11 is a perspective side view of a connector assembly formed after injection of the second-shot material.

FIG. 11 is a perspective side view of an connector assembly formed after injection of the second-shot material. The side view of FIG. 11 corresponds to the view of core element 2*b* in FIG. 6. Circuit member 40 has been trimmed in the manner discussed above to achieve the necessary isolation between pads. This view further illustrates an additional bore 190, which may be integrally formed by a protrusion provided within the cavity of the bottom portion 150 or top portion 172 of the mold. This type of bore is provided to allow for tightening of the set-screws after a lead is insert into a respective lead receptacle such as receptacle 200 in this instance. This bore will be fitted with a stop member such as a grommet and/or a washer to form a fluid-tight opening that is adapted to receive a tool used during the tightening of the set-screw to the lead pin or ring connector. In one embodiment, other apertures 202*a* and 202*b* are provided to allow the connector to be sutured to tissue within the implant cavity. This type of aperture may be formed by a pin that extends between the bottom portion 150 and top portion 172 of the mold assembly.

Figure 12:
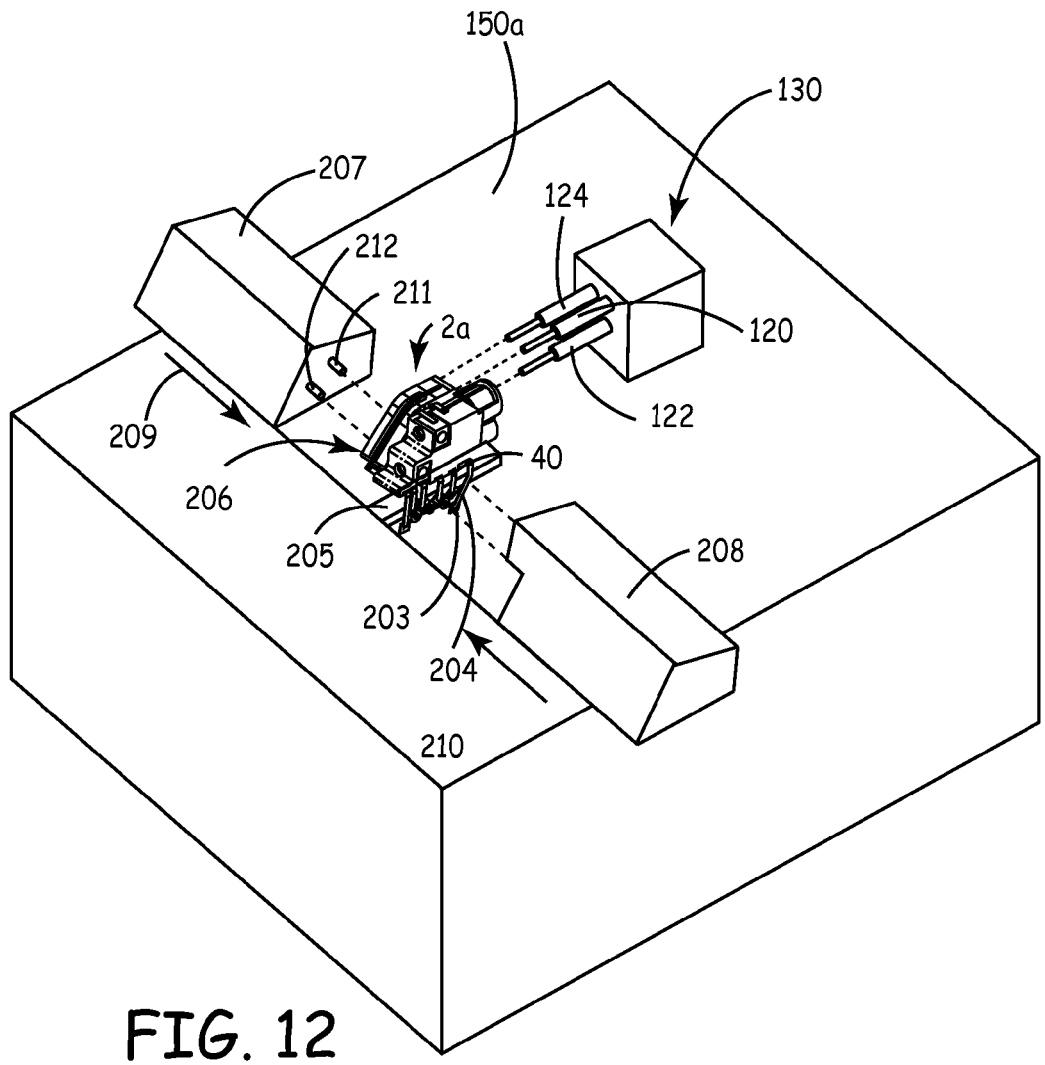
FIG. 12 is an alternative embodiment of the second-shot mold assembly of FIG. 9.

FIG. 12 is an alternative embodiment of the second-shot mold assembly of FIG. 9. This view illustrates core element 2*a*, the associated metal piece parts that have been loaded into the core member, and circuit member 40. This loaded core element assembly is then positioned in the bottom portion 150*a* of the second-shot mold fixture. In a manner similar to that discussed above with respect to FIG. 9, apertures provided within the circuit element may be positioned over pins 203 and 204 of shoulder member 205 to properly align and suspend core member over cavity 206 of the mold. Two slidable members 207 and 208 are provided to move into position around the core element assembly, as shown by arrows 209 and 210, respectively. These slidable members may be adapted to slide within tracks of the bottom portion 150*a*. Each of the slidable members includes one or more pegs such as pegs 211 and 212 of slidable member 207 to engage the set-screw block apertures so that additional bushings 140 through 146 (FIG. 9) are not needed. The slidable members provide additional stability during the second-shot injection mold process, and make removal of the connector assembly following the second-shot injection process less difficult.

Also shown in FIG. 12 is lead core assembly 130, which may be slidably positioned within the bottom portion 150*a* of the mold as illustrated by arrow 211 to engage the connector members of the core element 2*a* in the manner discussed above. Once the lead core assembly 130 and slidable members 207 and 208 are in position, a top portion of the mold which is similar to top portion 172 (FIG. 9) may be positioned over the bottom portion 150a. This top portion is held in position by a press or other mechanism during the second-shot injection process, as discussed above.

Figure 13:
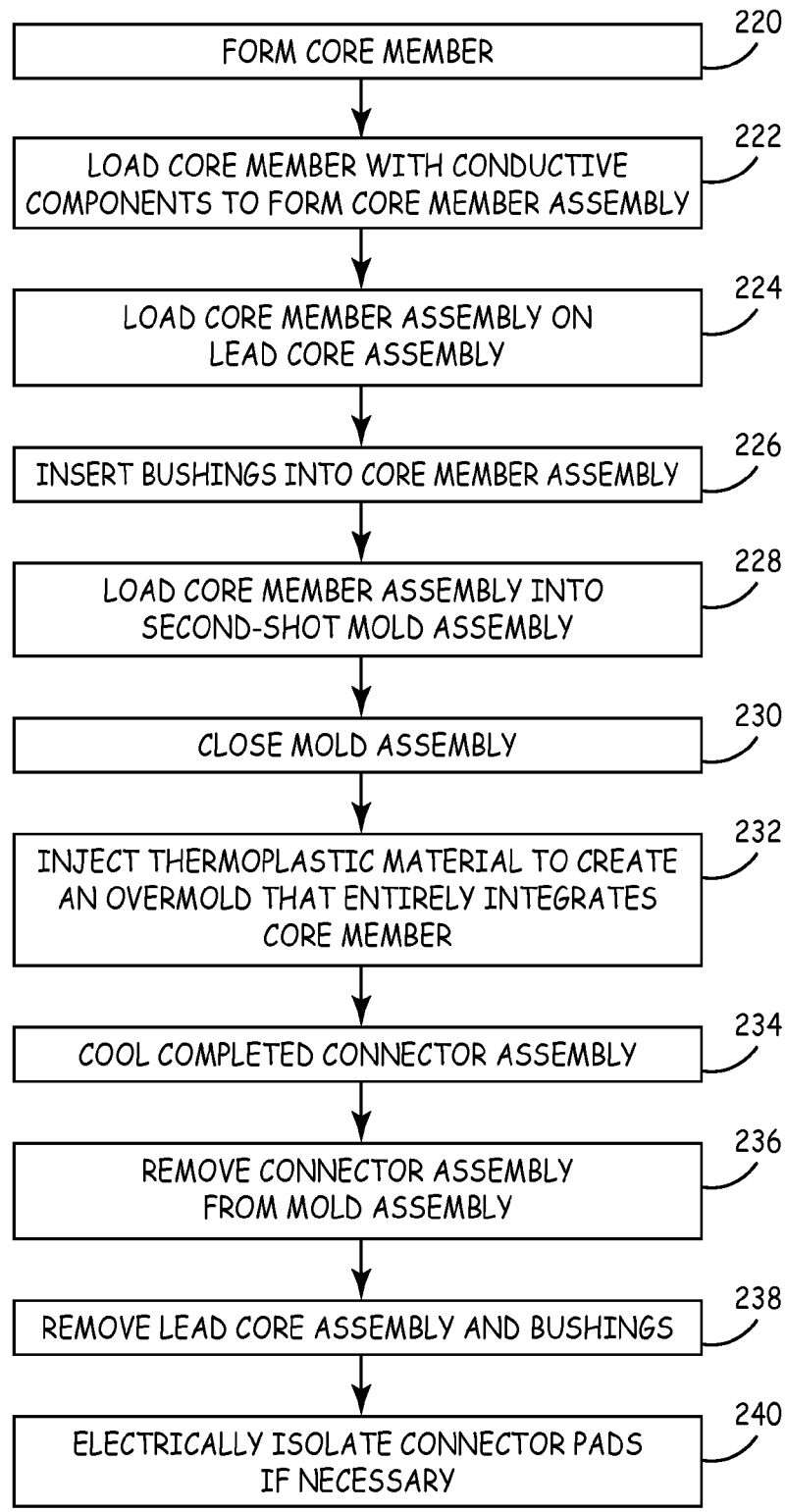
FIG. 13 is a flowchart of an assembly process.

FIG. 13 is a flowchart indicating the steps utilized to make a connector assembly. Although for discussion purposes the associated description involves the core element of FIG. 1, it will be understood the described process is equally applicable to the production of any connector type, or an entirely different type of thermoplastic component. In step 220, core member 2 is created. This may be accomplished by injecting a thermoplastic material into a primary mold assembly, or by fabricating a core member such as by a machining process. In step 222, the core member is loaded with the various conductive components such as the set-screw blocks and connector members to form the core member assembly. This step includes welding or solder the circuit member 40 to the various other conductive components. Processing continues with step 224, wherein the core member assembly is loaded onto the lead core assembly. Additional bushings may be inserted into set-screw blocks in 226 to ensure these structures remain open during the overmolding process, although this step is unnecessary if protrusions adapted to be inserted in the set-screw blocks are included in the second-shot mold assembly.

Next, in step 228, the core member assembly is loaded into the bottom portion 150 of the second-shot mold assembly. If desired, apertures in the circuit member 40 may be used to align the core member assembly within the mold cavity in a manner discussed above. The top portion 172 of the mold assembly is positioned over the bottom portion 150 as indicated by step 230, and the two portions are held together using a press, for example. Processing continues with step 232, wherein the thermoplastic material is injected to create the overmold. To bond the core member 2 with the overmold material, it is critical to heat the core member adequately. This may be accomplished by ensuring the mass of the core member is as small as possible as compared to the mass of the overmold material. In one embodiment, the mass of the core element is less than fifty percent of the mass of the overmolding material, and is preferably less than thirty percent of the overmold mass, as is discussed above. The bonding process may further be enhanced by preheating the core element prior to the overmold process, or by utilizing a thermoplastic material that can be heated to a relatively high temperature without altering the material characteristics. In either of these instances, the core element may have a mass that is greater than fifty percent of the overmold process while still achieving adequate bonding.

The connector assembly is cooled in step 234, and then removed from the mold assembly in step 236. The lead core assembly and optional bushings may be removed in step 238, and the various connector pads of the circuit member may be electrically isolated, as by removing interconnecting ones of the conductive traces. This is illustrated in step 240. As noted above, if individual circuit elements are used, this step is not needed.

Figure 14:
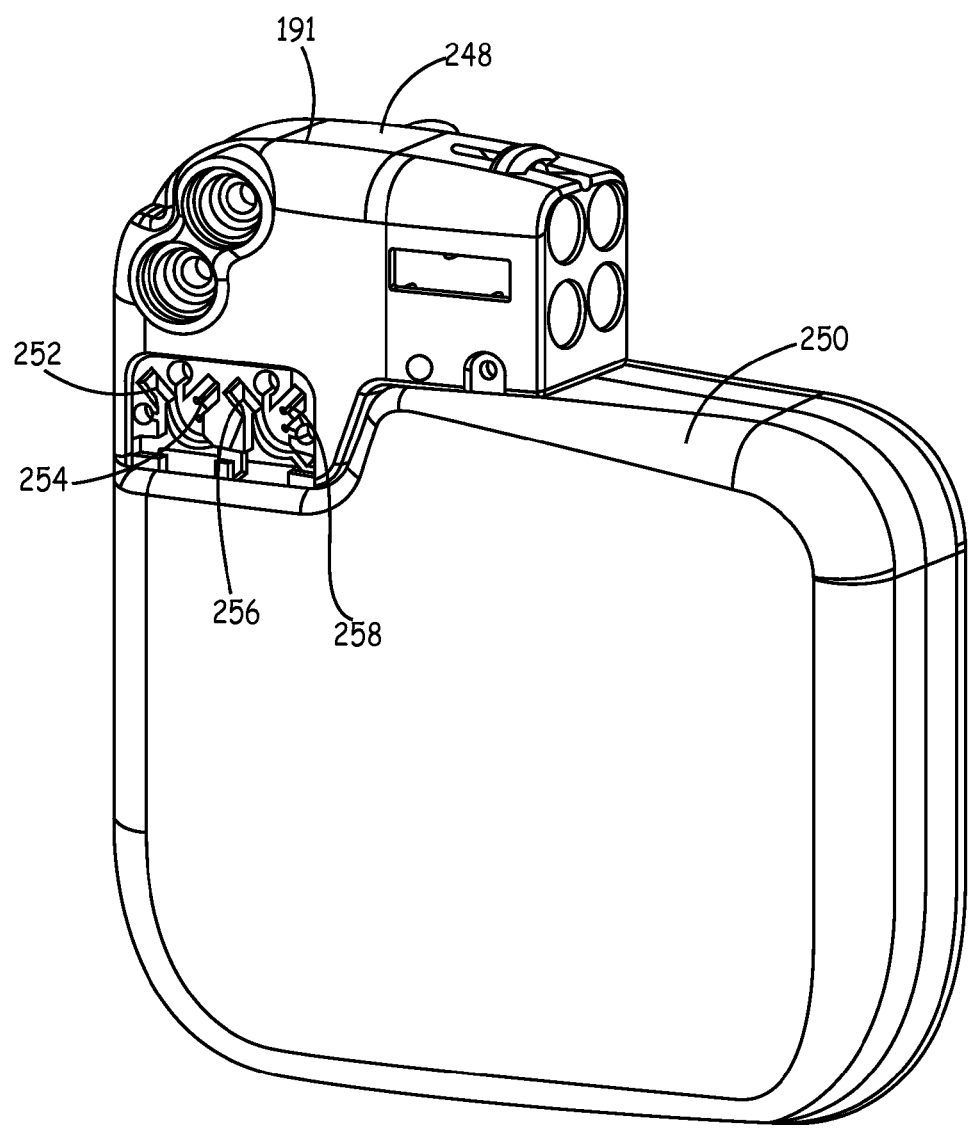
FIG. 14 is a side perspective view of a completed connector assembly coupled to an implantable medical device (IMD).

FIG. 14 is a side perspective view of a completed connector assembly 248 which is similar to that shown in FIG. 11. Connector assembly 248 is coupled to an implantable medical device (IMD) 250, which may be a pacemaker, cardio/defibrillator, neurological pain stimulator, or any other type of implantable medical device utilizing medical electrical leads. In one embodiment, the connector pads such as pads 252 through 258 of the connector assembly 248 are welded or soldered to a feedthrough pattern of the IMD. This provides the desired electrical connections between the connector assembly and the IMD.

Figure 15:
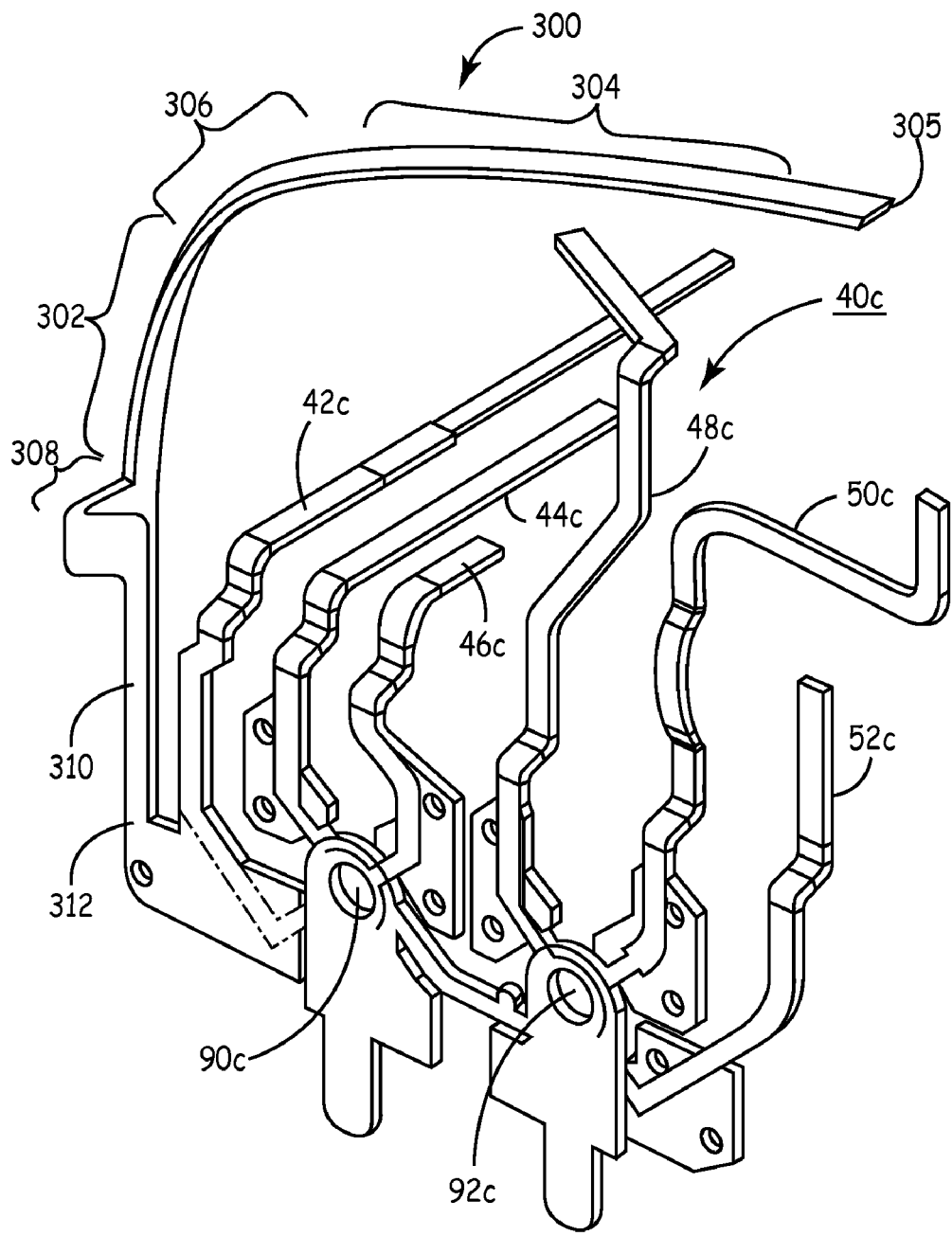
FIG. 15 is side perspective view of an alternative embodiment of the circuit member.

FIG. 15 is side perspective view of an alternative embodiment of the circuit member. In this view, like features of circuit member 40c as compared to circuit member 40 of FIGS. 1 through 4 are designated with like numeric identifiers including an additional suffix. Circuit member 40c includes a telemetry antenna 300 adapted to be positioned, for example, externally on the surface of the core element prior to the second-shot overmolding step. Telemetry antenna 300 includes a wire member curved to have a substantially 90 degree bend 306 into orthogonally extending first and second telemetry antenna segments 302 and 304. The second telemetry antenna segment 304 extends from the substantially 90 degree bend 306 to a wire member free end 305. The first telemetry antenna segment 302 extends from the substantially 90 degree bend 306 to a lateral wire member bend 308 over to a finger element 310, which extends to a fixed end 312, joining antenna 300 to the remainder of circuit member 40c.

When the circuit member 40c is assembled with a core member, the finger elements 310 and 42c through 52c are electrically and mechanically joined to make the assembly process more efficient. Circuit member 40c is soldered or welded to the various metal piece parts associated with a core element, such as set screw block and connector members as described previously in conjunction with FIGS. 1-4. By including antenna 300 in a single circuit member 40c with other conductive finger elements 42c-52c, the initial assembly process of the overall connector assembly is made easier since multiple elements need not be loaded onto the core element.

Figure 16:
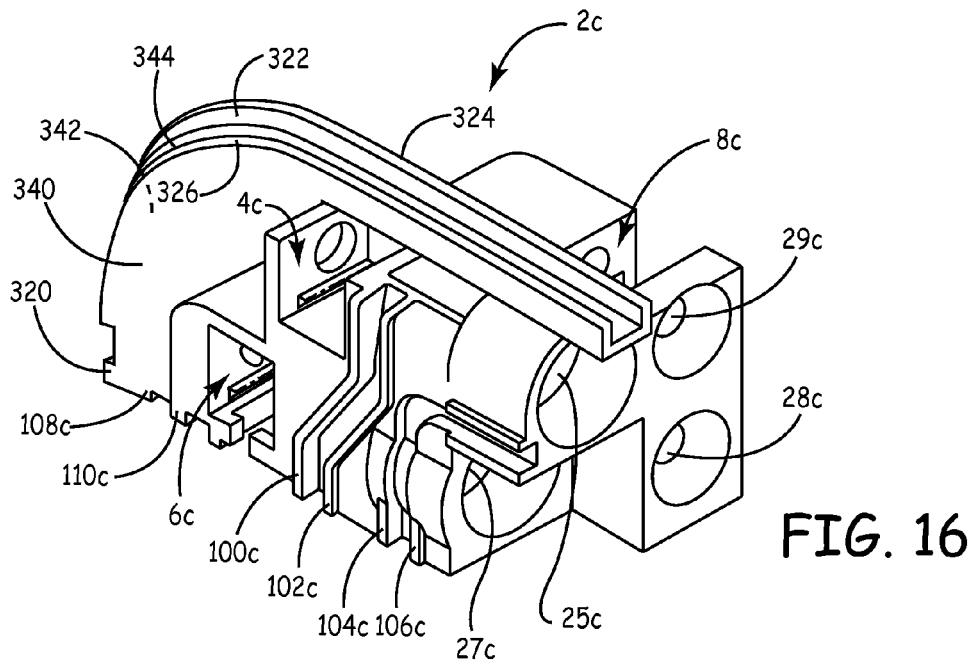
FIG. 16 is a side perspective view of a core element adapted to engage the circuit member of FIG. 15.

FIG. 16 is a side perspective view of a core element 2c adapted to engage the circuit member 40c of FIG. 15. As in FIG. 15, like features of core element 2c as compared to core element 2 of FIGS. 1 through 4 are designated with like numeric identifiers including an additional suffix. Core element 2c includes channel guides such as channel guides 100c through 110c that are provided to guide the finger elements of circuit member 40c into the desired position on the surface of core element 2c. Core element 2c further includes a channel guide 320 for guiding the lateral bend portion 308 (FIG. 15) of the telemetry antenna 300 (FIG. 15). The outer surfaces of core element 2c include a first and second major sides 340 and 342 separated by a curvilinear minor side 344. Curvilinear minor side 344 is provided with flanges 324 and 326 forming an outer channel 322 therebetween. Outer channel 322 is adapted to receive telemetry antenna 300 shown in FIG. 15. During the second-shot overmolding process, channel guide 320 and outer channel 322 retain the telemetry antenna in position and prevent shorts between the antenna and other finger elements of the circuit member.

Figure 17:
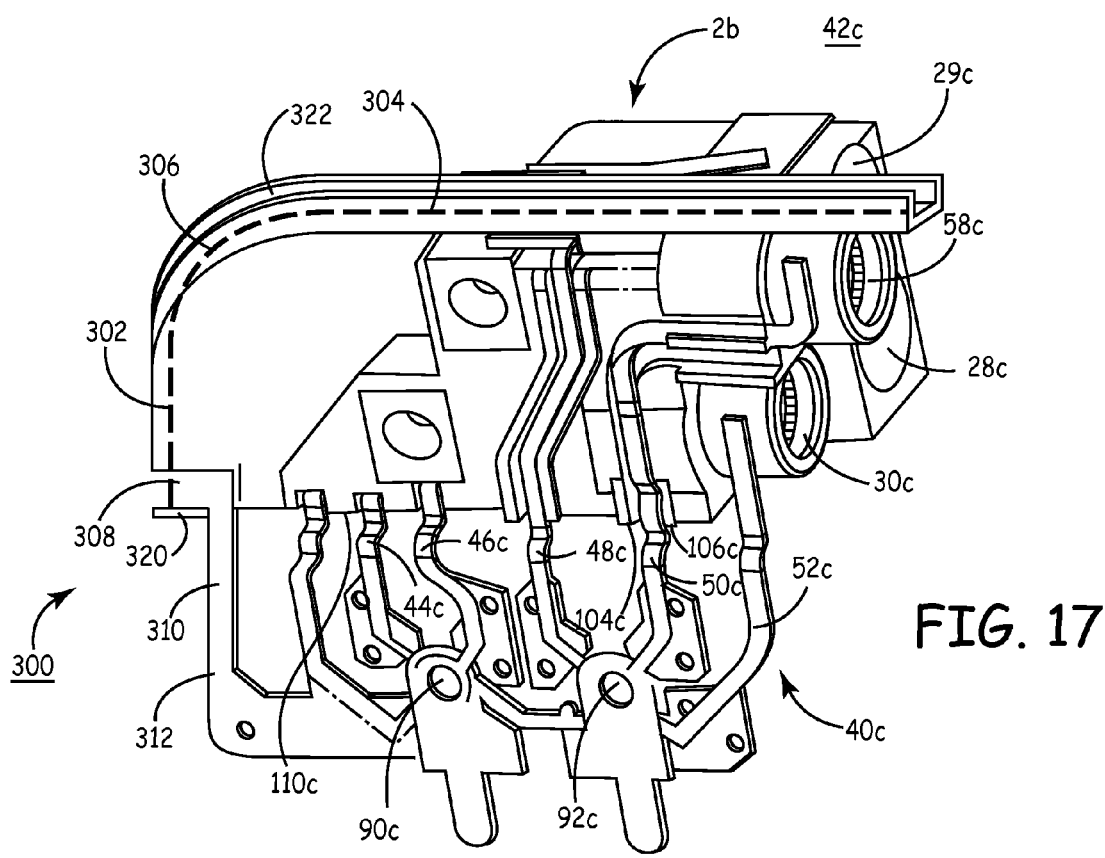
FIG. 17 is a side perspective view of the circuit member of FIG. 15 positioned on the surface of the core element of FIG. 16.

FIG. 17 is a side perspective view of circuit member 40c positioned on the surface of core element 2c. This figure illustrates the manner in which the telemetry antenna 300 is positioned over the core member 2c. Lateral wire member bend 308 is positioned along channel guide 320 and antenna elements 302, 304 and 306 (indicated by dashed line in the view of FIG. 17) are positioned along outer channel 322. Telemetry antenna free end 305 is supported in outer channel 322. After all conductive components have been inserted into the core element 2c and the circuit member 40c has been welded, soldered, or otherwise fixed into place, the resulting core element assembly 42c may be prepared to undergo the second-shot overmolding process as discussed above.

Following the injection of the overmold material, the individual finger elements or connector pads of the circuit member 40c maybe separated by cutting or trimming intervening conductive traces. The finger individually isolated elements/connector pads may then be electrically coupled to respective circuits included in an implantable medical device. For example, the finger elements/connector pads included in circuit member 40c are welded or soldered to a feedthrough pattern of the IMD. This provides the desired electrical connections between the connector assembly 42c and the IMD. In particular, antenna finger element 310 becomes electrically coupled to telemetry circuitry contained within IMD.

Figure 18:
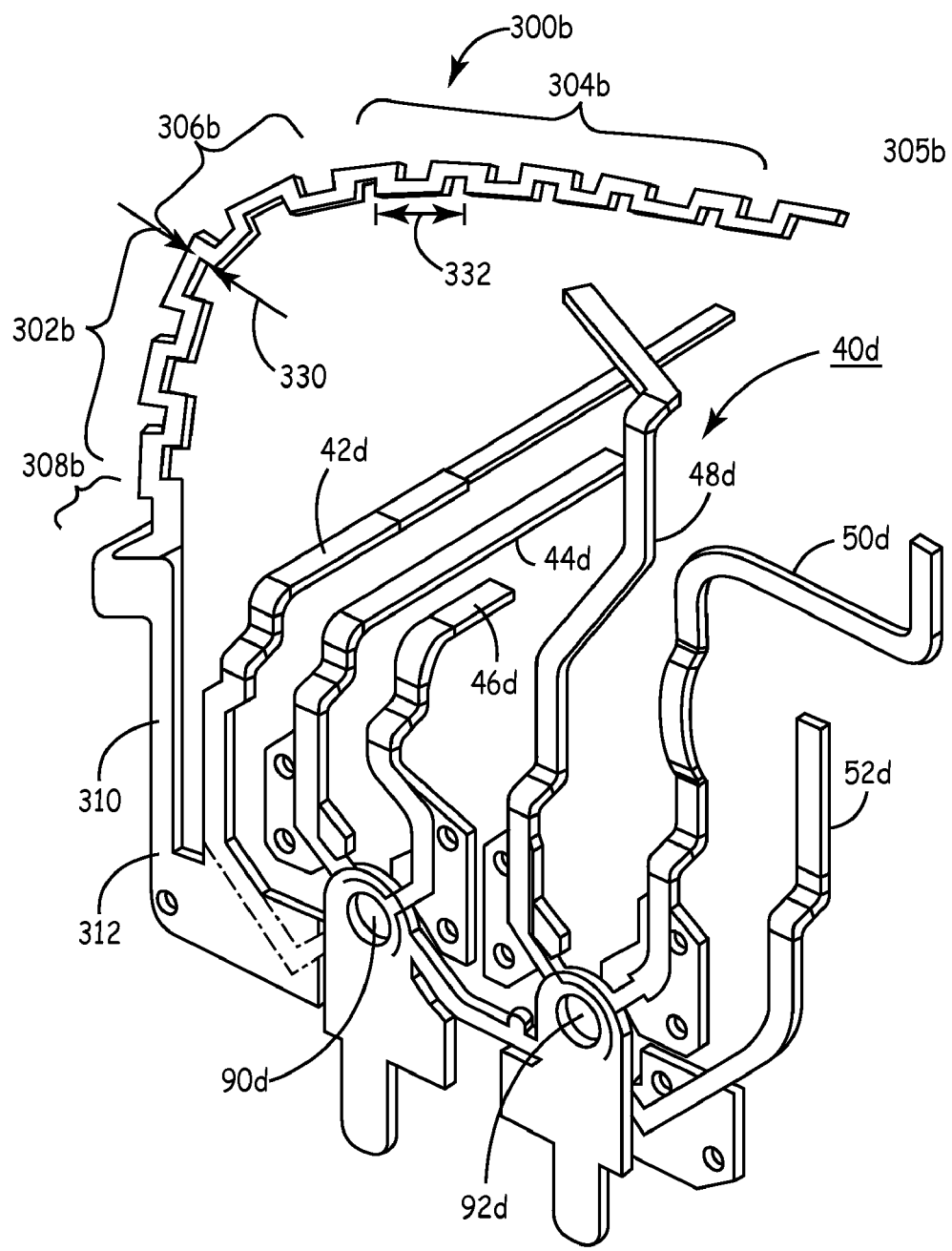
FIG. 18 is a side perspective view of an alternative embodiment of the circuit member including a serpentine antenna structure.

FIG. 18 is a side perspective view of an alternative embodiment of the circuit member. In this view, like features of circuit member 40d as compared to circuit member 40c of FIG. 15 are designated with like numeric identifiers including an additional suffix. This embodiment includes a serpentine telemetry antenna 300b having first and second elements 302b and 306b and bend 308b fabricated as a continuous wire member having a width 330 formed into a serpentine configuration having a pitch 332. Pitch 332 is defined as the distance between two subsequent similar points along the serpentine windings, e.g., peak to peak as illustrated. The width 330 and pitch 332 are selected to achieve the desired length of telemetry antenna 300b. Telemetry antenna 300b is provided with a total length corresponding to the wavelength of a driving signal for distance telemetry. Generally, an antenna length of at least one-fourth to one-half the wavelength of the driving frequency is desired and the length is generally an integral multiple of the half wavelength of the driving frequency. The serpentine configuration of telemetry antenna 300b allows antenna 300b to be provided with a longer overall length than the generally straight wire member elements shown in FIG. 15. The width of the outer channel of a corresponding core element is provided to appropriately accommodate the serpentine telemetry antenna 300b. Serpentine telemetry antenna configurations are generally disclosed in U.S. Patent Publication No. 2005/0203584, incorporated herein by reference in its entirety. The serpentine telemetry antenna 300b may be positioned along the outer channel 322 of core element 2c (shown in FIG. 16) in a similar manner to the positioning of the wire member antenna 300 as discussed above and shown in FIG. 17.

Figure 19:
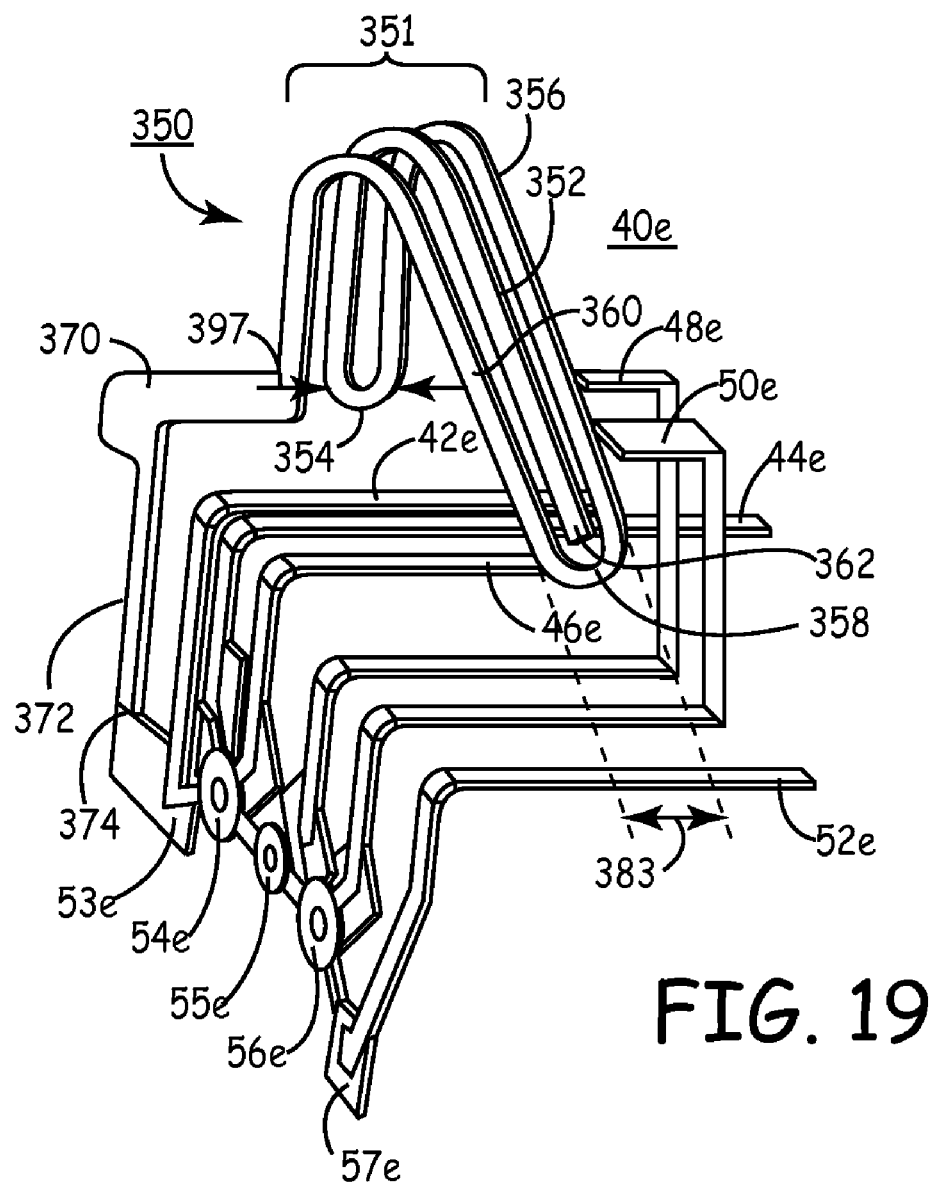
FIG. 19 is a perspective view of an alternative embodiment of the circuit member including a coiled antenna structure.

FIG. 19 is a perspective view of an alternative embodiment of the circuit member. In this view, like features of circuit member 40e as compared to circuit member 40 of FIG. 1 are designated with like numeric identifiers including an additional suffix. Circuit member 40e includes a telemetry antenna 350 configured in an elongated or generally flat coil. Telemetry antenna 350 is formed as a wire member including substantially parallel segments 352, 356, and 360 with intervening turns 354 and 358. Antenna 350 and other antenna configurations described herein may be formed by die cutting or punching the wire member in the configuration desired. In other embodiments, folded or bent antenna structures may be included in the circuit member.

Telemetry antenna 350 includes a curve 351 corresponding to a curvilinear side of a core element adapted to engage circuit member 40e as will be described below. In the configuration shown in FIG. 19, telemetry antenna 350 includes a first parallel segment 352, a penultimate turn 354 forming a substantially 180-degree turn, a penultimate parallel segment 356, a final turn 358 forming a substantially 180-degree turn, and a final parallel segment 360.

First parallel segment 352 extends between penultimate turn 354 and a free end 362 and is positioned between penultimate parallel segment 356 and final parallel segment 360. Final turn 358 is provided having a greater turn width 393 than the turn width 397 of penultimate turn 354. Telemetry antenna 350 further includes lateral bend 370 extending from final parallel segment 360 to a finger element 372 extending to fixed end 374.

Antenna 350 is shown having two turns 354 and 358 thereby creating three parallel segments 352, 356, and 360. It is recognized that telemetry antenna 350 could include additional turns and parallel segments, such as having three turns thereby forming four parallel segments and so on. The parallel segments are separated by sequentially increasing turn widths, to form the generally flat or elongated coil antenna configuration shown. The parallel segments 352, 356, and 360 are substantially straight between the turns 354 and 358 but may be formed with parallel curves, e.g. curve 351 between the turns 354 and 358 for shaping the antenna to conform to a core element outer surface. It is also recognized that a telemetry antenna including two parallel segments could be substituted for the antenna shown in FIG. 19.

Figure 20:
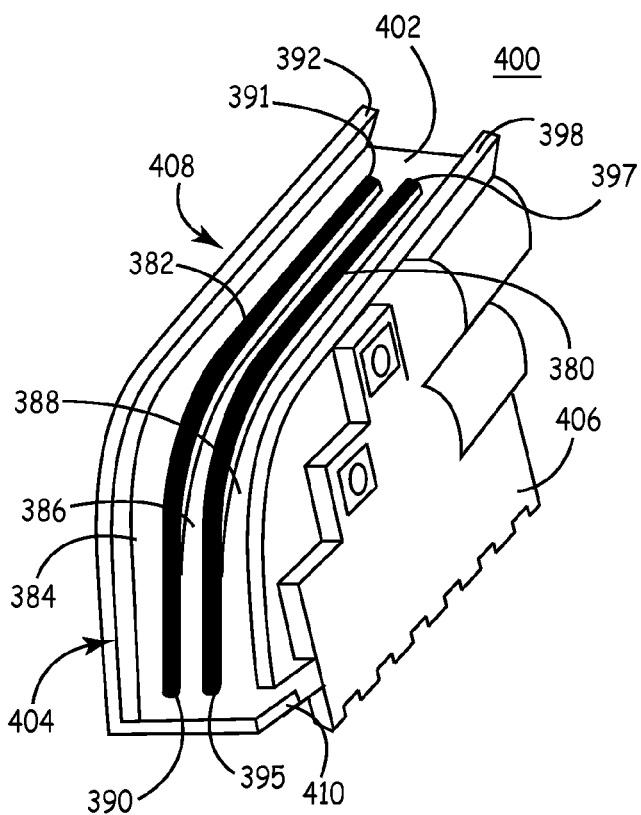
FIG. 20 is a top perspective view of a core element adapted to engage the circuit member of FIG. 19.

FIG. 20 is a top perspective view of a core element 400 adapted to engage circuit member 40e. Core element 400 includes first and second major sides 406 and 408 separated by a curvilinear minor side 404. Major sides 406 and 408 include various receptacles and apertures for receiving connector members, set screw blocks, circuit member finger elements, etc., which are not shown in full detail in FIG. 20 for the sake of simplicity, but may generally correspond, for example, to those included in core element 2 shown in FIG. 2. Curvilinear minor side 404 is formed having a first flange 392 and a second flange 398 forming an outer channel 402 therebetween for receiving the telemetry antenna. Outer channel 402 includes first and second antenna guides 380 and 382 extending along at least a portion of curvilinear minor side 404 between, and substantially parallel to, flanges 392 and 398. First antenna guide 380 extends between a first end 395 and a second end 397, and second antenna guide 382 extends between a first end 390 and a second end 391. Outer channel 402 and antenna guides 380 and 382 form three grooves 384, 386, and 388 therebetween for receiving telemetry antenna 350. A guide 410 is provided for guiding a lateral bend of the telemetry antenna.

Figure 21:
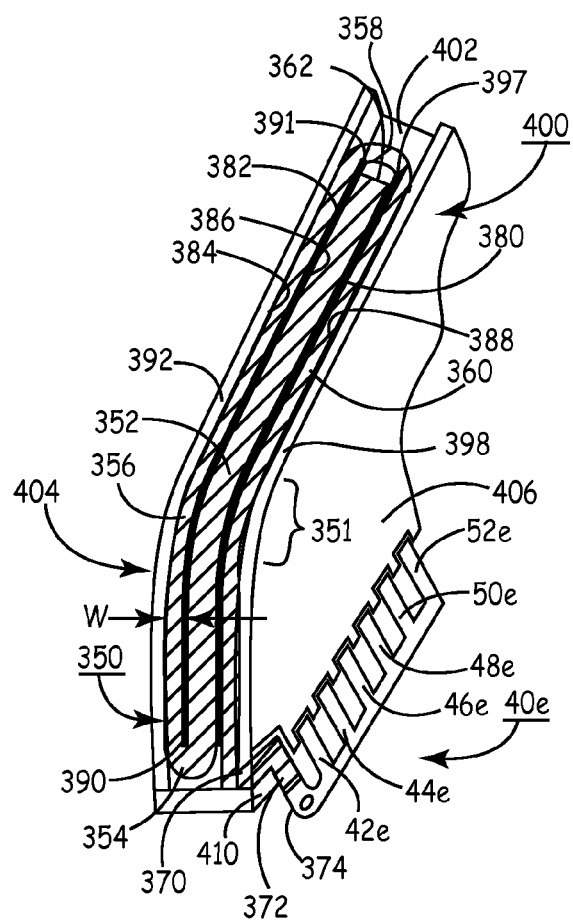
FIG. 21 is perspective view of a circuit member positioned on the surface of core element the core element of FIG. 20.

FIG. 21 is perspective view of circuit member 40e positioned on the surface of core element 400. In particular, telemetry antenna 350 is shown positioned along the outer channel 402 of core element 400. The free end 362 and first parallel segment 352 of telemetry antenna 350 are positioned between antenna guides 380 and 382 in the middle groove 386. Penultimate turn 354 wraps around the first end 390 of antenna guide 382. Penultimate parallel segment 356 is positioned between antenna guide 382 and outer channel flange 392, in groove 384. Final turn 358 wraps around second end 391 of antenna guide 382 and second end 397 of antenna guide 380. The final parallel segment 360 of telemetry antenna 350 is positioned between antenna guide 380 and outer channel flange 398 in groove 388. Parallel segments 352, 356, and 360 of antenna 350 are thus positioned to extend longitudinally along curvilinear side 404 of core element 400. The width W of the wire member material used to form telemetry antenna 350 and the widths 393 and 397 (shown in FIG. 19) of penultimate and final turns 354 and 358 are selected to fit within the limitations of the width of outer channel 402 of curvilinear side 404.

The remaining finger elements 42e through 52e may extend over the outer surface along major side 406 or into core element 400 through individual apertures to enable connection of finger elements 42e through 52e to the various set screw blocks, connector members, etc. assembled in core element 400. Positioning of finger elements 42e through 52 may generally correspond to the configurations described above, e.g. as in FIGS. 1-4.

Figure 22:
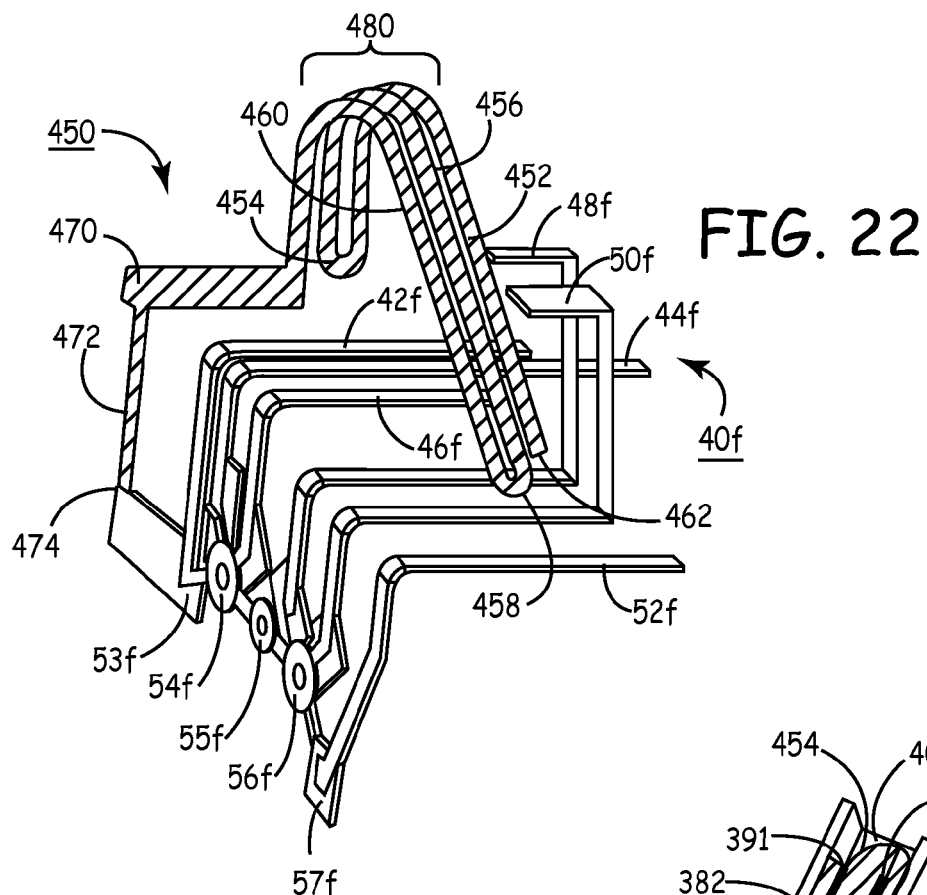
FIG. 22 is a perspective view of an alternative embodiment of a circuit member including an elongated serpentine telemetry antenna.

FIG. 22 is a perspective view of an alternative embodiment of a circuit member including an elongated serpentine telemetry antenna. In this view, like features of circuit member 40f as compared to circuit member 40 of FIG. 1 are designated with like numeric identifiers including an additional suffix. Circuit member 40f includes a telemetry antenna 450 formed from a continuous wire member. Antenna 450 is formed by cutting or punching the wire member in an elongated serpentine pattern as compared to the flat coil configuration of antenna 350 of FIG. 19. First parallel segment 452 extends from free end 462 to penultimate turn 454 and is positioned adjacent penultimate parallel segment 456. Penultimate parallel segment 456 extends between penultimate turn 454 and final turn 458, and is positioned adjacent final parallel segment 460. Penultimate turn 454 and final turn 458 are provided with substantially equal turn widths to form the elongated serpentine pattern. Parallel segments 452, 456 and 460 are substantially straight between turns 454 and 458 but do include parallel curves to form bend or curve 480 for conforming to the curvilinear minor side of the core element. Telemetry antenna 450 further includes lateral bend 470 extending from final parallel segment 460 to a finger element 472 extending to fixed end 474.

Figure 23:
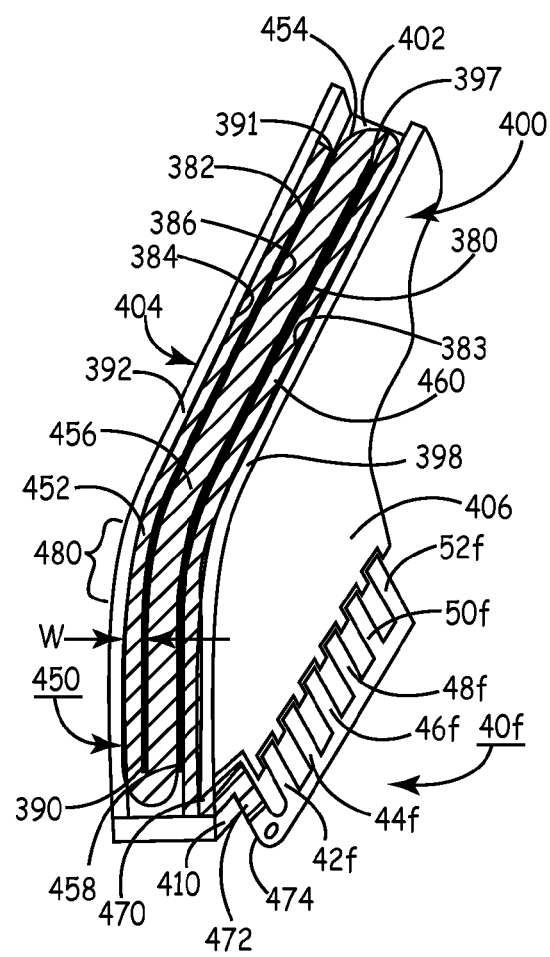
FIG. 23 is a top perspective view of the circuit member of FIG. 22 positioned on the surface of a core element.

FIG. 23 is a top perspective view of circuit member 40f positioned on the surface of core element 400 shown in FIG. 20. The first parallel segment 452 of telemetry antenna 450 is positioned between antenna guide 382 and outer channel flange 392 in groove 384. Penultimate turn 454 wraps around a first end 390 of antenna guide 382. Penultimate parallel segment 456 is positioned between antenna guide 382 and antenna guide 380 in grove 386. Final turn 458 wraps around second end 397 of antenna guide 380. Final turn 458 is provided having a turn width substantially equal to the turn width of penultimate turn 454. The final parallel segment 360 is positioned between antenna guide 380 and outer channel side 398. Parallel segments 352, 356, and 360 are thus positioned to extend longitudinally along a majority of the length of curvilinear minor side 404 of core element 400. The width W of the wire member material used to form telemetry antenna 450 and the widths of penultimate and final turns 454 and 458 are selected to fit within the limitations of the width of curvilinear side 404 formed with outer channel 402.

The width W of the wire member used to from the antenna, the number and width of the turns and the number of parallel segments will be determined according to a particular application. Telemetry antennas 350 and 450 shown in FIGS. 19 and 22, respectively, are provided with a total length corresponding to the wavelength of a driving signal for distance telemetry. As described above, an antenna length is generally at least one-fourth to one-half the wavelength of the driving frequency and generally an integral multiple of the half wavelength of the driving frequency. The configurations of telemetry antennas 350 and 450 allow the antenna to be provided with a longer overall length than a generally straight wire member antenna as shown in FIG. 15.

While antennas 350 and 450 are shown extending over the curvilinear minor side of the core element 400, it is recognized that an antenna structure included in a circuit member assembled with a core element may be adapted to conform to any outer non-conductive surface of the core element, for example along either of major sides 406 or 408 of core element 400 shown in FIG. 20.

Figure 24:
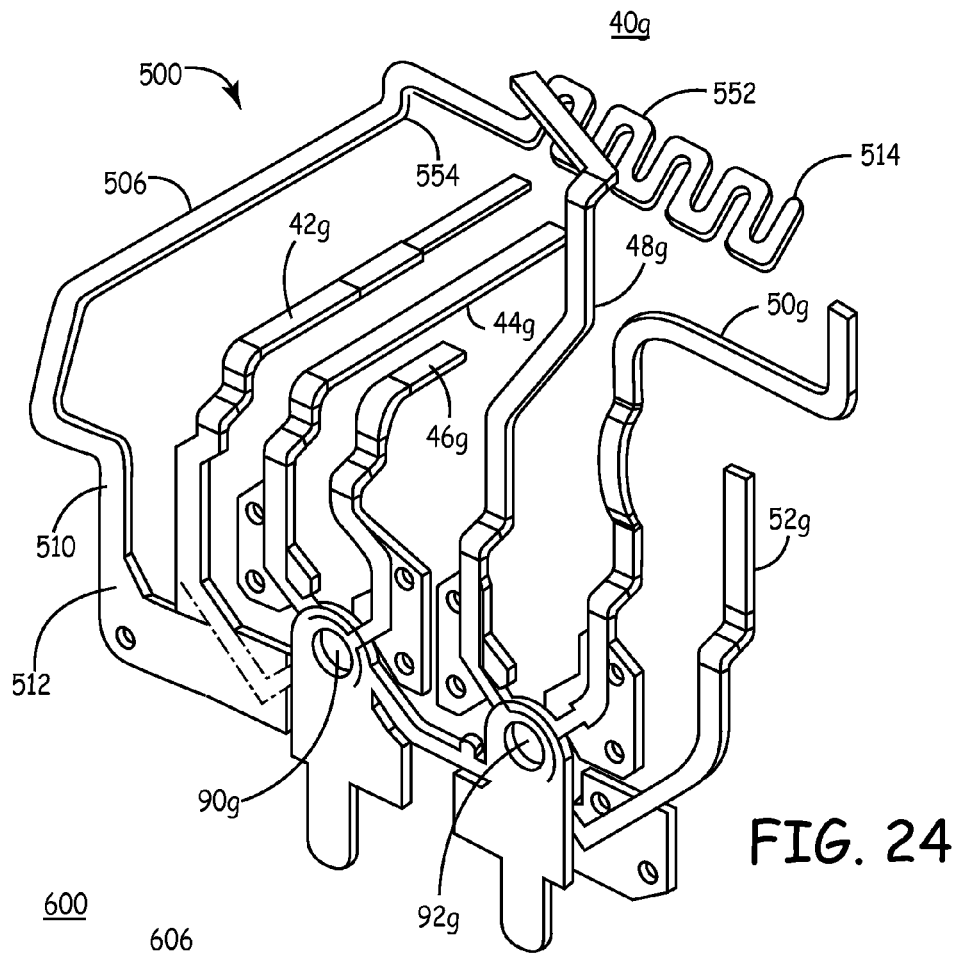
FIG. 24 is a side perspective view of an alternative embodiment of the circuit member including a telemetry antenna adapted to extend along a major side of a core element.

FIG. 24 is a side perspective view of an alternative embodiment of the circuit member including a telemetry antenna adapted to extend along a major side of a core element. In this view, like features of circuit member 40g as compared to circuit member 40 of FIGS. 1 through 4 are designated with like numeric identifiers including an additional suffix. Circuit member 40g includes a telemetry antenna 500 adapted to be positioned externally on a major side outer surface of the core element prior to the second-shot overmolding step. Telemetry antenna 500 includes a wire member bent at a substantially 90 degree bend 504 for conforming to an outer surface of the core element and to direct an antenna segment 502 along the surface of a major side of the core element. Antenna segment 502 is shown in a serpentine configuration extending from bend 504 to free end 514. Antenna 500 further includes a lateral segment 506 extending from a finger element 510 to bend 504. Finger element 510 terminates at fixed end 512 where antenna 500 is joined to the remainder of circuit member 40g.

Figure 25:
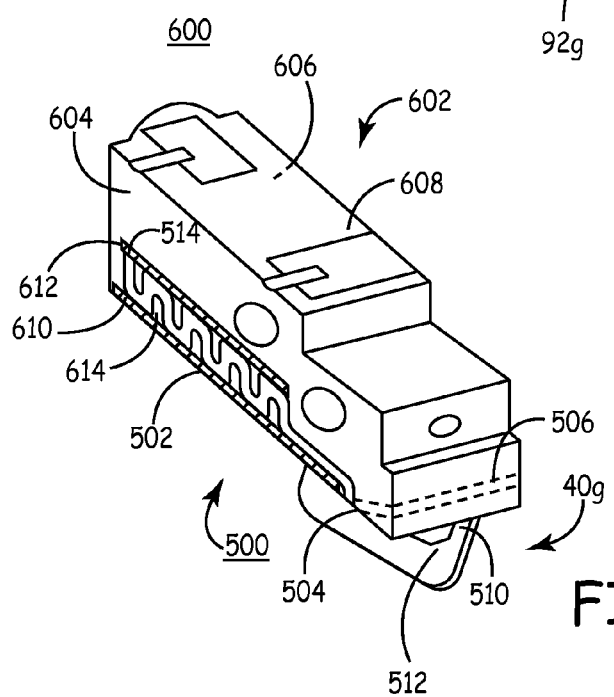
FIG. 25 is a perspective view of the circuit member shown in FIG. 24 assembled with a core element adapted to engage the circuit member to form an assembly.

FIG. 25 is a perspective view of the circuit member 40g assembled with a core element 602 adapted to engage circuit member 40g to form assembly 600. Core element 602 includes various receptacles and apertures for receiving connector members, set screw blocks, circuit member finger elements, etc., which are not shown in full detail in FIG. 25 for the sake of simplicity, but may generally correspond, for example, to those included in core element 2 shown in FIG. 2. Core element 602 includes first and second major sides 604 and 606 separated by a minor side 608. An outer channel 614 is formed between first and second flanges 610 and 612 extending from major side 604.

Circuit member 40g is positioned along core element 602. Antenna lateral segment 506 extends along core element 602 and bend 504 conforms to the outer surface of core element 602 to position antenna segment 502 along major side 604. Serpentine antenna segment 502 extends from bend 504 within outer channel 614 to antenna free end 514.

Figure 26:
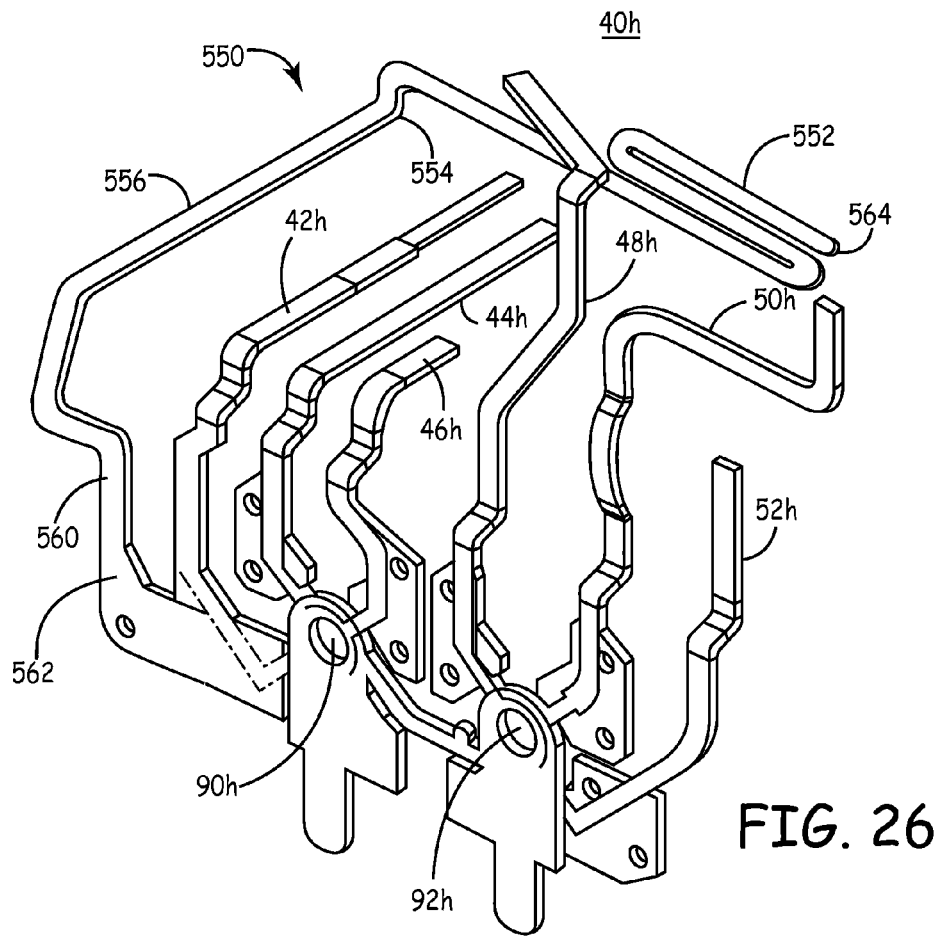
FIG. 26 is a side perspective view of an alternative embodiment of the circuit member including an elongated serpentine telemetry antenna adapted to extend along a major side of the core element.

FIG. 26 is a side perspective view of an alternative embodiment of the circuit member including a telemetry antenna adapted to extend along a major side of the core element. In this view, like features of circuit member 40h as compared to circuit member 40 of FIGS. 1 through 4 are designated with like numeric identifiers including an additional suffix. Circuit member 40h includes a telemetry antenna 550 adapted to be placed externally on a major side outer surface of the core element prior to the second-shot overmolding step. Telemetry antenna 550 includes a wire member bent at a substantially 90 degree bend 554 for conforming to an outer surface of the core element and to direct antenna segment 552 along the outer surface of a major side of the core element. Antenna segment 552 is shown in an elongated serpentine configuration. In an alternative embodiment, antenna segment 552 may be formed in a flat coil pattern as described previously in conjunction with FIG. 19. Antenna 550 further includes a lateral segment 556 extending from a finger element 560 to bend 554. Finger element 560 terminates at fixed end 562 where antenna 550 is joined to the remainder of circuit member 40h.

Figure 27:
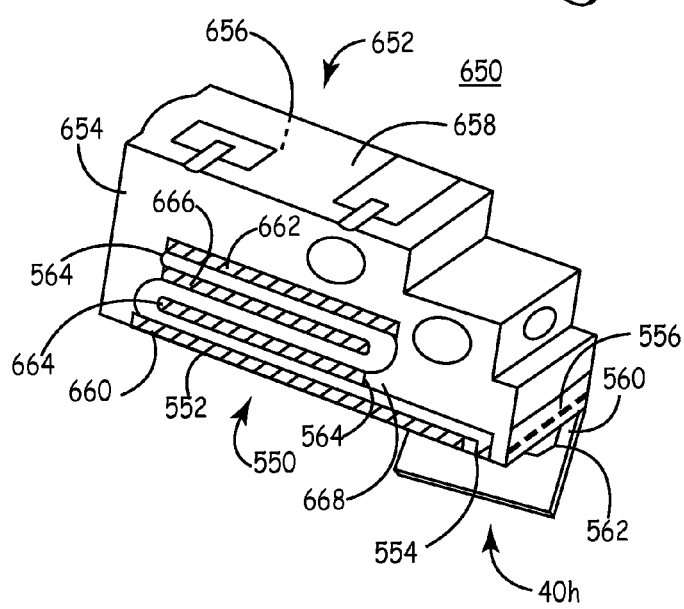
FIG. 27 is a perspective view of the circuit member shown in FIG. 26 assembled with a core element adapted to engage the circuit member to form an assembly.

FIG. 27 is a perspective view of the circuit member 40h assembled with a core element 652 adapted to engage circuit member 40h to form assembly 650. Core element 652 includes various receptacles and apertures for receiving connector members, set screw blocks, circuit member finger elements, etc., which are not shown in full detail in FIG. 27 for the sake of simplicity, but may generally correspond, for example, to those included in core element 2 shown in FIG. 2. Core element 652 includes first and second major sides 654 and 656 separated by a minor side 658. Core element 652 further includes first and second flanges 660 and 662 forming an outer channel 668 for positioning antenna segment 552. Antenna guides 664 and 666 extend between and substantially parallel to flanges 660 and 662.

Circuit member 40h is positioned along core element 652. Antenna lateral segment 556 extends along core element 652 and bend 554 conforms to the outer surface of core element 652. Antenna segment 552 extends from bend 554 along major side 654 within outer channel 666 to antenna free end 564. Antenna guides 664 and 666 extend substantially parallel to flanges 660 and 662 to support and maintain the position of antenna segment 552 during the overmolding process and prevent shorts between parallel segments of antenna 550.

Although the above description discusses a particular type of connector assembly adapted to couple to four leads having particular types of connectors, it may be noted that the inventive process may be adapted to manufacture any type of connector assembly having any number of shapes and sizes, and that is adapted to couple to any type of lead connector. Alternatively, the process could be utilized to manufacture any other type of thermoplastic component that is adapted to include conductive piece parts. Thus, the description of the specific connector assembly set forth above should be considered merely illustrative in nature.

The invention claimed is:

1. A connector assembly to be coupled to an implantable medical device, comprising:
   a core element formed of a first thermoplastic material shaped to receive a connector member for receiving a lead, the core element having an outer surface;
   a circuit member positioned adjacent to the core element, the circuit member including a portion extending along the core element to the connector member and including an antenna structure extending over a portion of the core element outer surface; and
   an overmold portion formed of a second thermoplastic material to extend over and adhere to the core element.

2. The connector assembly of claim 1 wherein the antenna structure includes a curve portion corresponding to the portion of the core element outer surface.

3. The connector assembly of claim 1 wherein the core element outer surface comprises a first major side, a second major side and a curvilinear minor side separating the first major side and the second major side and wherein the antenna structure extends along the curvilinear minor side.

4. The connector assembly of claim 1 wherein the core element outer surface comprises a first flange and a second flange and wherein the antenna structure extends between the first and second flanges.

5. The connector assembly of claim 1 wherein the antenna structure is a wire member antenna.

6. The connector assembly of claim 5 wherein the antenna structure is formed having a free end, a fixed end, a first turn, a first segment extending between the free end and the first turn, a final turn, and a final segment extending from the final turn substantially parallel to the first segment.

7. The connector assembly of claim 6 wherein the antenna structure includes a penultimate turn and a penultimate segment extending from the first turn to the penultimate turn substantially parallel to the first and second segments.

8. The connector assembly of claim 6 wherein the first turn having a first turn width and the final turn having a second turn width substantially equal to the first turn width.

9. The connector assembly of claim 6 wherein the first turn having a first turn width and the final turn having a second turn width greater than the first turn width.

10. The connector assembly of claim 7 wherein the antenna structure is formed in a flat coil structure corresponding to the first segment being positioned between the penultimate and final segments.

11. The connector assembly of claim 7 wherein the antenna structure is formed in an elongated serpentine structure corresponding to the penultimate segment being positioned between the first and final segments.

12. The connector assembly of claim 1 wherein the core element outer surface comprises a first major side, a second major side and a curvilinear minor side separating the first major side and the second major side and wherein the antenna structure extends along one of the first major side and the second major side.

* * * * *